(12) United States Patent
Kochergin et al.

(10) Patent No.: US 6,836,578 B2
(45) Date of Patent: Dec. 28, 2004

(54) SYSTEM AND METHOD FOR MEASURING PHYSICAL STIMULI USING VERTICAL CAVITY SURFACE EMITTING LASERS WITH INTEGRATED TUNING MEANS

(75) Inventors: Vladimir Kochergin, Westerville, OH (US); Philip Swinehart, Westerville, OH (US)

(73) Assignee: Lake Shore Cryotronics, Inc., Westerville, OH (US)

( * ) Notice: Subject to any disclaimer, the term of this patent is extended or adjusted under 35 U.S.C. 154(b) by 0 days.

(21) Appl. No.: 10/740,602

(22) Filed: Dec. 22, 2003

(65) Prior Publication Data

US 2004/0202400 A1 Oct. 14, 2004

Related U.S. Application Data

(63) Continuation-in-part of application No. 10/412,671, filed on Apr. 14, 2003.

(51) Int. Cl.[7] .............................. G02B 6/26; H01S 3/10
(52) U.S. Cl. .......................................... 385/12; 372/20
(58) Field of Search .............................. 385/12, 16, 24; 372/20

(56) References Cited

U.S. PATENT DOCUMENTS

| | | | |
|---|---|---|---|
| 4,136,566 A | 1/1979 | Christensen | |
| 4,355,910 A | 10/1982 | Quick et al. | |
| 4,761,073 A | 8/1988 | Meltz et al. | |
| 4,778,987 A | 10/1988 | Saaski et al. | |
| 4,806,012 A | 2/1989 | Meltz et al. | |
| 5,202,939 A | 4/1993 | Belleville et al. | |
| 5,291,502 A | 3/1994 | Pezeshki et al. | |
| 5,359,681 A | 10/1994 | Jorgenson et al. | |
| 5,380,995 A | 1/1995 | Udd et al. | |
| 5,392,117 A | 2/1995 | Belleville et al. | |
| 5,401,956 A | 3/1995 | Dunphy | |
| 5,629,951 A | 5/1997 | Chang-Hasnain et al. | |
| 5,646,401 A | 7/1997 | Udd | |
| 5,771,253 A | 6/1998 | Chang-Hasnain et al. | |
| 5,798,521 A | 8/1998 | Froggatt | |
| 5,809,050 A | * 9/1998 | Baldwin et al. | ............... 372/43 |
| 5,815,278 A | 9/1998 | Johnston et al. | |
| 6,024,488 A | 2/2000 | Wu et al. | |
| 6,122,305 A | 9/2000 | Putnam et al. | |
| 6,141,098 A | 10/2000 | Sawatari et al. | |
| 6,204,920 B1 | 3/2001 | Ellerbrock et al. | |
| 6,233,263 B1 | 5/2001 | Chang-Hasnain et al. | |
| 6,301,274 B1 | 10/2001 | Tayebati et al. | |
| 6,438,149 B1 | 8/2002 | Tayebati et al. | |
| 2003/0218753 A1 | * 11/2003 | Reuter | ........................ 356/445 |

OTHER PUBLICATIONS

Data sheet, MetroFlex Tunable Optical Transmitters, 2 pages (Jul. 26, 2001).

(List continued on next page.)

*Primary Examiner*—Akm Enayet Ullah
*Assistant Examiner*—Tina M Lin
(74) *Attorney, Agent, or Firm*—Nixon & Vanderhye P.C.

(57) ABSTRACT

An optical sensor diagnostic system utilizes a tunable Vertical Cavity Surface Emitting Laser (VCSEL) that incorporates an integrated MEMS tuning mechanism provides variable wavelength light into an optical fiber with improved wavelength scanning speed and greater simplicity of construction. Sensors, such as Bragg gratings, are disposed along the fiber in the light path. Each sensor reflects or transmits light exhibiting a characteristic amplitude and/or phase feature with respect to wavelength, the wavelength position of which is affected by an environmental stimulus imposed thereon. The light reflected or transmitted through each sensor is mixed with light passed through an optical reference path and then converted to an electrical signal by a simple detector and monitored by ciruitry that applies signal processing to the detected power spectral distribution, by this means providing output signals indicative of the environmental stimulus on each sensor.

76 Claims, 13 Drawing Sheets

OTHER PUBLICATIONS

News release, "Bandwidth9 Unveils Industry's First VCSEL–Based, Tunable Optical Transmitter Module for Metro DWDM Applications" (Jan. 4, 2001).

News release, "Bandwidth9 Announces Plans to Develop MetroFlex™ Tunable Optical Filters for Use in DWDM Metropolitan Area Networks" (Feb. 8, 2001).

Press Release listing, http://www.bw9.com.

Vakhshoori, D. et al., "2mW CW singlemode operation of a tunable 1550 nm vertical cavity surface emitting laser with 50 nm tuning range," *Electronics Letters*, vol. 35 No. 11, pp. 900–901 (May 27, 1999).

Larson, M.C. et al., "Wide and continuous wavelength tuning in a vertical–cavity surface–emitting laser using a micromachined deformable–membrane mirror," *Appl. Phys. Lett.* 68(7), pp. 891–893 (Feb. 12, 1996).

Archambault, Jean–Luc et al., "Fiber Gratings in Lasers and Amplifiers," *Journal of Lightwave Technology*, vol. 15, No. 8, pp. 1378–1390 (Aug. 1997).

Duck, G., et al., CWF68 "High resolution and high speed distributed in–fiber Bragg grating strain measurements," Wednesday Afternoon, CLEO'99, pp. 295–296 (May 26, 1999).

Chang–Hasnain, Connie J., "Tunable VCSEL," *IEEE Journal on Selected Topics in Quantum Electronics*, vol. 6, No. 6, pp. 978–987 (Nov./Dec. 2000).

Chan, C.C., et al., "Investigation of unwanted interferometric signals ina fiber Brag grating sensor using a tunable laser and a first derivative interrogation technique," *Optics Communications*, pp. 203–210 (Jan. 1, 2000).

Ball, G.A., et al., "Fiber Laser Source/Analyzer for Bragg Grating Sensor Array Interrogation," *Journal of Lightwave Technology*, vol. 12, No. 4 pp. 700–703 (Apr. 1994).

Measures, R.M. et al., "Tunable laser demodulation of various fiber Bragg grating sensing modalities," *Smart Mater., Struct.* 7, pp. 237–247 (1998).

Chan, Chi Chiu, et al., "Performance Analysis of a Time–Division–Multiplexed Fiber Bragg Grating Sensor Array by Use of a Tunable Laser Source," *IEEE Journal of Selected Topics in Quantum Electronics*, vol. 6, No. 5, pp. 741–749 (Sep./Oct. 2000).

Hsu, Kevin, "Continuously Tunable Photopumped 1.3– m Fiber Fabry–Perot Surface–Emitting Lasers," *IEEE Photonics Technology Letters*, vol. 10, No. 9, pp. 1199–1201 (Sep. 1998).

Coldren, Larry A., "Monolithic Tunable Diode Lasers," *IEEE Journal on Selected Topics in Quantum Electronics*, vol. 6, No. 6, pp 988–999 (Nov./Dec. 2000).

Harris, James S., "Tunable Long–Wavelength Vertical–Cavity Lasers: The Engine of Next Generation Optical Networks?," *IEEE Journal on Selected Topics in Quantum Electronics*, pp. 1145–1160, vol. 6, No. 6 (Nov./Dec. 2000).

Chow, Weng W. et al., "Design, Fabrication, and Performance of Infrared and Visible Vertical–Cavity Surface–Emitting Lasers," *IEEE Journal of Quantum Electronics*, pp. 1810–1824, vol. 33, No. 10 (Oct. 1997).

Chang–Hasnain, Connie J. et al., "MEMS cantilevers precisely adjust cavity thickness to yield broadly tunable VCSELs" *OE Magazine*, The Monthly Publication of SPIE—The International Society for Optical Engineering (May 2001).

Kersey, A.D., et al. [10$^{th}$ Optical Fiber Sensors Conference, Glasgow, Oct. 1994, pp. 53–56].

Kretschmann and Raether, Z. Naturforsch. Teil A 23:2135–2136, 1968).

Fontana et al., Applied Optics 27:3334–3339, 1988).

Liedberg et al., "Surface Plasmon Resonance for Gas Detectionand Biosensing," Sensors and Actuators 4:299–304, 1983.

Daniels et al. "Surface Plasmon Resonance Applied to Immunosensing," Sensors and Actuators 15:11–17, 1988.

Jorgenson et al., [IEEE/Engineering Medicine and Biology Society. Proceedings 12:440–442, 1990]),.

Gent et al., [Applied Optics 29:2843–2849, 1990]).

Matsubaru et al., [Applied Optics 27:1160–1163, 1988].

Homola J., et al., "Novel polarization control scheme for spectral surface plasmon resonance sensors," Sensors and Actuators B, B51 (1–3), Aug. 1998, p. 331–339.

Kabashin A.V. et al., "Surface plasmon resonance bio–and chemical sensors with phase–polarisation contrast," Sensors and Acuators B, B54 (1–2), Jan. 1999, pp. 51–56.

Larson, M.C. and Harris Jr, J. S., "Wide and continuous wavelength tuning in a vertical–cavity surface–emitting laser using a micromachined deformable–membrane mirror," Appl. Phys. Lett. 68 (7), Feb. 1996 pp. 891–893.

* cited by examiner

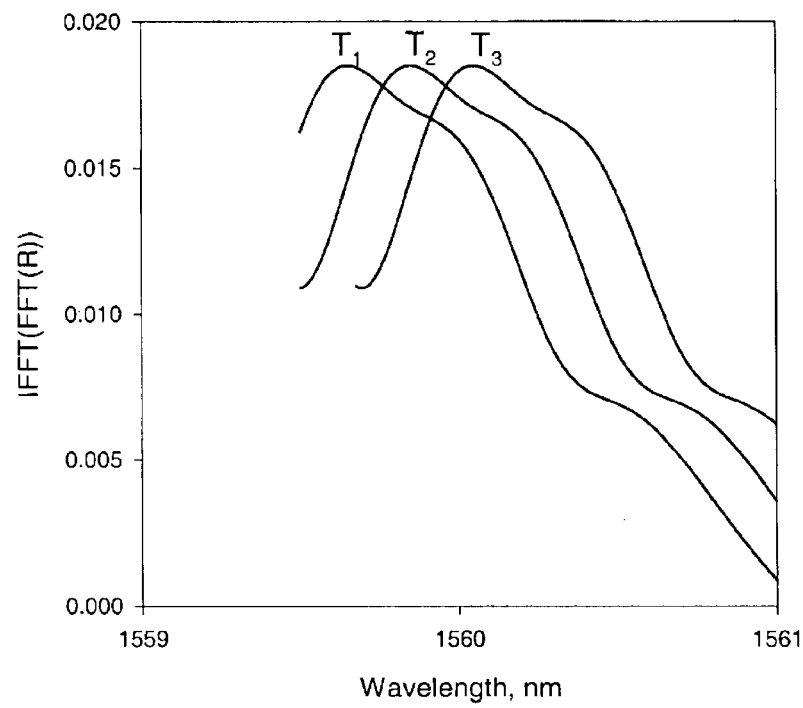
*Fig. 6C*
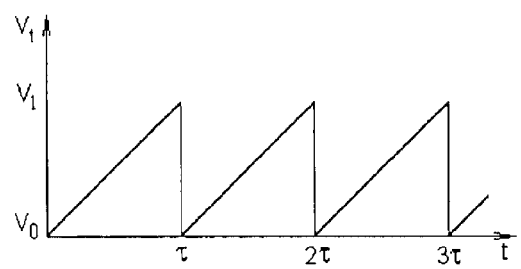 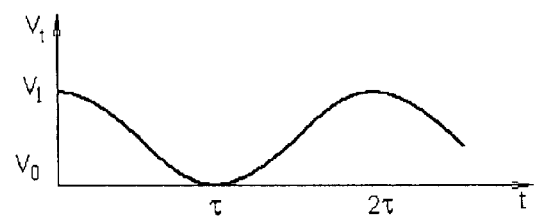
*Fig.7A*  *Fig.7C*

SYSTEM AND METHOD FOR MEASURING PHYSICAL STIMULI USING VERTICAL CAVITY SURFACE EMITTING LASERS WITH INTEGRATED TUNING MEANS

CROSS-REFERENCES TO RELATED APPLICATIONS

This application is a continuation-in-part of application Ser. No. 10/412,671, filed Apr. 14, 2003, which application claims the benefit of application Ser. No. 09/983,999, filed Oct. 26, 2001, now U.S. Pat. No. 6,549,687, which applications are hereby incorporated by reference.

STATEMENT REGARDING FEDERALLY SPONSORED RESEARCH OR DEVELOPMENT

Not applicable.

FIELD

The technology herein relates to systems using vertical cavity, surface emitting lasers (VCSELs), and more particularly to such VCSELs having integrated MEMS (microelectromechanical) wavelength tuning means to interrogate optical sensors. Still more particularly, the technology herein relates to such systems for use in interrogating fiber and planar Bragg gratings and etalons sensitive to physical stimuli, and to specific system configurations for use with such Bragg grating and etalon sensing devices.

BACKGROUND AND SUMMARY

Fiber optic sensors employing measurement of the shift of wavelength position of a sensor's spectral peculiarity (maximum, minimum or some other function) under the influence of a physical stimulus are well known to those skilled in the art. Examples of such sensors include Bragg grating-based strain, pressure, temperature and current (via the associated magnetic fields) sensors and Fabry-Perot (FP) etalon pressure, temperature and strain sensors to name a few. Unfortunately, the widespread use of such sensors has generally been restricted in the marketplace because of many well known problems, including the susceptibility of simple, inexpensive sensing systems to optical noise and the great expense of most of the solutions found to overcome said susceptibility.

We have, in contrast, discovered that combining a new type of laser, a vertical cavity, surface emitting laser (VCSEL), with an integrated microelectromechanical (MEMS) tuning mechanism as an interrogating instrument with sensors of many different types will enable new, less expensive and more reliable class of optical sensor systems.

As is well known, a Bragg grating is a series of optical elements that create a periodic pattern of differing indices of refraction in the direction of propagation of a light beam. A Bragg grating is generally formed in an optical fiber by means of exposing ultraviolet sensitive glass (usually germanium doped fiber) with an ultraviolet (UV) beam that varies periodically in intensity, usually accomplished by means of an interference pattern created by a phase mask or a split beam, such as with a Lloyd's mirror apparatus. Planar Bragg gratings are created by exposing "photoresist" of any of a number of types through a phase shift or other type of mask, or holographic exposure, or they can be written directly with an electron beam. Light reflections caused by the periodic index of refraction pattern in the resulting grating interfere constructively and destructively. Since the refractive index contrast between UV-exposed and unexposed sections of fiber is small but the number of sections is very large, the reflected beam narrows its spectrum to a sharp peak, as narrow as a fraction of a nanometer in spectral width. In addition, the phase spectral dependences of the reflected and transmitted light generally exhibit some modification around the wavelength of said reflection peak.

It is known that Bragg gratings patterned into optical fibers or other waveguides may be used to detect physical stimuli caused by various physical parameters, such as, for example, strain, pressure, temperature, and current (via the associated magnetic fields) at the location of the gratings. See for example U.S. Pat. Nos. 4,806,012 and 4,761,073 both to Meltz, et al; U.S. Pat. No. 5,380,995 issued to E. Udd; U.S. Pat. No. 6,024,488 issued to J. Wu; and the publication authored by Kersey, A. D., et.al. [$10^{th}$ Optical Fiber Sensors Conference, Glasgow, October 1994, pp.53–56]. Generally, in such a sensor, the core and/or cladding of the optical fiber (or planar waveguide) is written with periodic grating patterns effective for selectively reflecting a narrow wavelength band of light from a broader wavelength band launched into the core (waveguide layer in the waveguide). The spectral positions of sharp maxima or minima in the reflected or transmitted light intensity spectra indicate the intensity of strain, temperature, pressure, electrical current, or magnetic field variations at the location of the grating. The mechanism of the spectral position variability lies in changes in either the grating period or the indices of refraction, or both, which can be affected by various environmental physical stimuli, such as, for example, temperature and pressure. Frequently, more than one stimulus or physical parameter affects the sensors at the same time, and compensation must be designed into the sensor or the measurement technique for all the variables but one (which can be accomplished by many physical, optical and electronic techniques known in the art). The typical sensitivity limits of fiber grating sensors in the current art are generally about 0.1° C. to 1° C. and/or 1 microstrain or higher (depending on the packaging and/or embedding of the sensor), respectively. Advantages of a spectral shift method of sensor interrogations include the high accuracy of wavelength determination (akin to the advantages of measuring frequency instead of magnitude) and immunity to "optical noise" due to fluctuations in fiber transmission amplitude (microbending losses, etc.). The use of Bragg gratings also allows the multiplexing of many sensors on the same fiber via wavelength dependent multiplexing techniques (WDM), e.g., dividing the total wavelength band into sections dedicated to individual sensors.

Another approach for the interrogation of fiber Bragg grating strain sensors has been disclosed by M. E. Froggatt, (U.S. Pat. Nos. 5,798,521 and 6,566,648, articles [Froggatt M., "Distributed measurement of the complex modulation of a photoinduced Bragg grating in an optical fiber", Applied Optics, 35 (25), pp. 5162–5164, September 1996] and [Froggatt M., Moore J., "Distributed measurement of static strain in an optical fiber with multiple Bragg gratings at nominally equal wavelengths", Applied Optics, 37 (10), pp. 1741–1746, April 1998]). This approach is based on an interferometric scheme (FP interferometer) utilizing a coherent optical source such as a continuously tunable laser with a very narrow wavelength range (over just 0.23 nm) and a discretely tunable laser (over 2.5 nm total). The Froggatt method utilizes Fourier transformation of the measured spectrum, filtering of the Fourier transform followed by inverse Fourier transformation. Such an approach permits the acquisition of phase information, which in turn permits the multiplexing of a large array of fiber Bragg gratings having the same wavelength position of their reflectance peaks (unlike WDM, where a different spectral position of the reflectance peak of each sensor is essential). Such a technique is known as Optical Frequency Domain Multiplexing (OFDM). Large numbers of multiplexed sensors (up to 22) have been demonstrated [Froggatt M., Moore J., "Distributed measurement of static strain in an optical fiber with multiple Bragg gratings at nominally equal wavelengths", Applied Optics, 37 (10), pp. 1741–1746, April 1998]. However, such a technique also may suffer from significant limitations. First, the nature of the laser used can make the detection scheme complex due to the necessity of using complex requirements for wavelength determination. Second, the accuracy and resolution of the instrument may be far from optimal due to the limited wavelength range of the laser that was specified. Third, the update rate of such an instrument may be quite slow due to both the slow tuning speed of the laser specified and the large computational overhead from the active wavelength determination scheme used, which in turn limited the accuracy of the instrument. Fourth, the detection range of these systems may be limited by the short coherence length of the laser. Fifth, the price of such a system may be very high compared to competitive electronic techniques, due both to the laser and the active wavelength determination scheme used. Despite the attractiveness of the Froggatt approach, it may be stated that this scheme has not reached wide market acceptance.

The precision, dynamic range and multiplexing capabilities of the alloptical sensor interrogation techniques reviewed above, other than OFDR, are generally defined in part by the spectral power of the light source, especially in cases in which a broadband source is used. The LEDs, SLDs (superluminescent diodes) and various lamps usually used provide spectral power that can be too little when divided into subnanometer-sized segments (average power divided by wavelength range). This limits critical parameters such as the magnitude of the reflected peak available to the optical sensor, causing lower-than-desirable signal-to-noise ratios. Another technique, the use of a conventional laser diode tuned with a motorized external cavity, electrical current or temperature mechanisms tends to be more effective because all the power of the laser is contained in a narrow beam as it is tuned across the spectrum. Several techniques have been proposed. One is the use of a conventional laser diode tuned with electrical current, which has been proposed by Dunphy et. al. (U.S. Pat. No. 5,401,956). Another is the use of a tunable fiber laser, which has been proposed by G. A. Ball et. al. [J. of Lightwave Technology, vol. 12, no. 4, April 1994 p 700]. When using a scanning laser technique, an inexpensive detector and electronics system simply and easily determines the wavelength at the peak (or null) of the reflected (or transmitted) light intensity against a known wavelength reference. However, past art approaches are generally too expensive, too slow, too unstable or too inaccurate to have a wide range of practical applications. Laser diodes tuned with their excitation current, while inexpensive and faster than thermal methods, suffer from narrow tuning wavelength spans and changing optical power, which may limit practical applications to only time division-multiplexed (TDM) Bragg sensors. The broadband light source method utilizes an inexpensive light source, but generally requires a spectrometer to read the signals (an optical spectrum analyzer may cost as much as $35,000). The broadband method is most practical when many sensors are multiplexed on the same fiber. Still, spectrometers are temperamental and not well suited to field use. The lasers tuned with external cavities that are now in use, on the other hand, typically are more expensive than spectrometers, but have the advantage of using an inexpensive detector. In addition, such lasers are typically slow to tune, such as 100 nm/sec, and may be even more delicate than spectrometers. Scanning (or tuning) speed is especially important in applications in which absorption and polarization related noise are significant because of the degrading effects these noise sources on the signal to noise ration (SNR). One the other hand, mass-produced MEMS-tunable VCSELs, configured as sensing instruments, are expected to cost at least an order of magnitude less than prior art lasers and be at least two orders of magnitude faster than prior art lasers.

Fiber etalon-based sensors (also known as Fabry-Perot sensors) are well known to those skilled in the art (see, for example, U.S. Pat. No. 5,646,401 issued to E. Udd). Etalons consist of two mirrored surfaces that may be internal or external to the optical fiber. The reflectivity of an etalon is defined by interference between light waves reflected from first and second mirrors (or reflecting surfaces). The advantages of etalon-based pressure, temperature and/or stain sensors include the low cost of etalons and very high sensitivity. However, with broadband light sources used for interrogation, measurements that are based on light intensity or count interference fringes are very susceptible to optical noise or other technical problems (e.g., losing count of the fringes), to the point of being impractical. The sole practical, self-calibrating system uses an optical cross-correlating interferometer as a detector, also an expensive technique (see, for example, U.S. Pat. Nos. 5,202,939 and 5,392,117 both issued to Belleville, et al.). However, the multiplexing of a number of sensors with such a technique (such as required for structural monitoring and many other applications) is impossible as far as is presently known.

A new kind of laser, a vertical cavity surface emitting laser (VCSEL), has recently been developed. Generally, VCSELs are made completely with wafer-level processing and the chips emit from the direction of the broad surface of the wafer, rather than having to be cleaved out of the wafer in order to have an exposed p-n junction edge from which to emit, as in older art. This enables another benefit to be designed into the wafer structure—tunability. This is done with micromachining (MEMS) technology by placing a stack of optical layers, forming a mirror, in front of the emitting surface in such a way that the stack can be varied in its distance from the emitting surface by piezoelectric, magnetic, electrostatic or some other micro-actuating means. The groups of C. J. Chang-Hasnain (US Patent, [IEEE J. on Selected Topics in Quantum Electronics, V 6, N 6, November 2000, p. 978]), J. S. Harris Jr. (U.S. Pat. No. 5,291,502, [Appl. Phys. Lett. 68 (7), February 1996 p. 891]), and Vakhshoori [Electronics Letters, May 1999, V. 35, N.11 p. 900] have shown the potential for making tunable VCSELs with MEMS tuning mechanisms with wide tuning ranges and fast tuning speeds combined with good coherence length (exceeding 2 meters) and extreme reliability of the tuner mechanism (it survives hundreds of megacycles). Tunable VCSELs are relatively simple to manufacture, exhibit continuous mode-hop-free tunability over a wide spectrum, and offer more than an order of magnitude lower cost as compared to prior art tunable lasers or optical spectrometers. Integrated, MEMS-tunable VCSELS make possible truly affordable and accurate optical sensor systems by combining low cost detectors and low cost excitation sources, one or the other of which is very expensive in the prior art systems with the accuracy and resolution considerably exceeding those of the prior art lasers.

We use such VCSEL technology in a novel way to provide a means of optical wavelength scanning Bragg grating and etalon resonance sensors of all types with integrated, MEMS-tunable VCSELs in order to measure various physical parameters at several orders of magnitude lower cost than prior art, with the added benefits of enhanced accuracy, ruggedness and reliability.

In more detail, an exemplary illustrative non-limiting arrangement provides a diagnostic system which interfaces with optical fibers or optical waveguides having Bragg grating or other types of sensors as described herein, embedded therein for the determination of static and dynamic values of various physical parameters, and, further, to provide means of guaranteeing wavelength accuracy during the scanning cycle.

In accordance with an illustrative non-limiting aspect of an exemplary non-limiting illustrative implementation, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a reflected light having an associated local amplitude and/or phase perturbation (for example, maximum or minimum). The wavelength at said minimum or maximum of amplitude varies in response to an environmental stimulus imposed upon the corresponding sensor. The tunable VCSEL individually illuminates each of the sensors throughout its associated wavelength band of an amplitude minimum or maximum. A reference fiber length (serving as a arm of an interferometer) is disposed between said VCSEL assembly and an optical sensor or sensor array. One or two reflection means are disposed in a reference fiber length to create a reference optical length in a fiber. A coupler or circulator must be provided to divert the optical signal reflected from the sensor array and the reflection means to the photodetector, the electrical signal from which is relayed to the control block circuitry and external electronic circuitry as required. The control block controls the laser temperature via a thermoelectric element or other means and may or may not adjust the laser power output according to a signal from a monitor phoitodiode, as required. A tuning controller provides a variable voltage or other signal to the tunable VCSEL indicative of the desired wavelength of the tunable light. A signal processor responsive to the electrical detection signal interprets a shift in the wavelength position of the magnitude minimum or maximum due to the environmental stimulus calculated from the recorded electrical detection signals, and provides a signal indicative of said stimulus.

In accordance with another illustrative aspect of an exemplary non-limiting illustrative implementation, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a reflected light having an associated local amplitude and/or phase perturbation (for example, maximum or minimum). The wavelength at said minimum or maximum of amplitude varies in response to an environmental stimulus imposed upon the corresponding sensor. The tunable VCSEL individually illuminates each of the sensors throughout its associated wavelength band of an amplitude minimum or maximum. A reference fiber length (serving as an arm of an interferometer) is disposed in a separate optical path from the path connecting said VCSEL assembly and an optical sensor or sensor array. One or two reflection means are disposed in a reference fiber length to create a reference optical length in a fiber. At least one coupler or circulator must be provided to divide the optical signal from the tunable VCSEL into the reference and sensing paths and to divert the optical signal reflected from the sensor array and from the reflection means in the reference path to the photodetector, the electrical signal from which is relayed to the control block circuitry and external electronic circuitry as required. The control block controls the laser temperature via a thermoelectric element or other means and may or may not adjust the laser power output according to a signal from a monitor photodiode, as required. A tuning controller provides a variable voltage or other signal to the tunable VCSEL indicative of the desired wavelength of the tunable light. A signal processor responsive to the electrical detection signal interprets a shift in the wavelength position of the magnitude minimum or maximum due to the environmental stimulus calculated from the recorded electrical detection signals, and provides a signal indicative of said stimulus.

In accordance with a further non-limiting aspect of an exemplary non-limiting illustrative, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a reflected light having an associated local amplitude and/or phase perturbation (for example, maximum or minimum). The wavelength at said minimum or maximum of amplitude varies in response to an environmental stimulus imposed upon the corresponding sensor. The tunable VCSEL individually illuminates each of the sensors throughout the sensor's associated wavelength band including as examples an amplitude minimum or maximum. A reference fiber length (serving as one arm of the Mach-Zander interferometer) is disposed in a separate optical path from the path connecting said VCSEL assembly and an optical sensor or sensor array. At least one coupler must be provided to divide the optical signal from the tunable VCSEL into the reference arm and sensing paths and to divert the optical signal reflected from the sensor array to another arm of said interferometer. Another coupler must be provided to combine the light from two arms of said interferometer and to direct said combined (interfering) light to the photodetector, the electrical signal from which is relayed to the control block circuitry and external electronic circuitry as required. The control block controls the laser temperature via a thermoelectric element or other means and may or may not adjust the laser power output according to a signal from a monitor photodiode, as required. A tuning controller provides a variable voltage or other signal to the tunable VCSEL indicative of the desired wavelength of the tunable light. A signal processor responsive to the electrical detection signal interprets a shift in the wavelength position of the magnitude minimum or maximum due to the environmental stimulus calculated from the recorded electrical detection signals, and provides a signal indicative of said stimulus.

According to a further exemplary non-limiting illustrative implementation, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a transmitted light having an associated local amplitude and/or phase perturbation (for example, maximum or minimum). The wavelength at said minimum or maximum of amplitude varies in response to an environmental stimulus imposed upon the corresponding sensor. The tunable VCSEL individually illuminates each of the sensors throughout the sensor's associated wavelength band including as examples an amplitude minimum or maximum. A reference fiber length (serving as a arm of an interferometer) is disposed in a separate optical path from the path connecting said VCSEL assembly, optical sensor or sensor array and optical detector. One or two reflection means may be disposed in a reference fiber length to create a reference optical length. An optical splitter (for example optical coupler) must be provided to divide optical signal from the tunable VCSEL into the reference and sensing paths. An optical combiner (for example another optical coupler) must be provided and combine the optical signal transmitted through the sensor array and through the reference path and to direct combined light to the photodetector, the electrical signal from which is relayed to the control block circuitry and external electronic circuitry as required. The control block controls the laser temperature via a thermoelectric element or other means and may or may not adjust the laser power output according to a signal from a monitor photodiode, as required. A tuning controller provides a variable voltage or other signal to the tunable VCSEL indicative of the desired wavelength of the tunable light. A signal processor responsive to the electrical detection signal interprets a shift in the wavelength position of the magnitude minimum or maximum due to the environmental stimulus calculated from the recorded electrical detection signals, and provides a signal indicative of said stimulus.

In accordance with a further aspect of an exemplary non-limiting illustrative implementation, an optical sensor diagnostic system includes an integrated MEMS-tunable VCSEL for providing a wavelength-tunable light in response to a voltage or other control signal, the tunable light being launched into an optical waveguide. At least one optical sensor, disposed in the path of the tunable light, provides a transmitted light having an associated local amplitude and/or phase perturbation (for example, maximum or minimum). The wavelength at said minimum or maximum of amplitude varies in response to an environmental stimulus imposed upon the corresponding sensor. The tunable VCSEL individually illuminates each of the sensors throughout the sensor's associated wavelength band including as examples an amplitude minimum or maximum. A reference fiber length (serving as a arm of an interferometer) is disposed between said VCSEL-assembly and an optical sensor or sensor array or between said optical sensor or sensor array and said detector. One or two reflection means are disposed in a reference fiber length to create a reference optical length in a fiber. The optical signal transmitted through the sensor array and the reference path is directed toward the photodetector, the electrical signal from which is relayed to the control block circuitry and external electronic circuitry as required. The control block controls the laser temperature via a thermoelectric element or other means and may or may not adjust the laser power output according to a signal from a monitor photodiode, as required. A tuning controller provides a variable voltage or other signal to the tunable VCSEL indicative of the desired wavelength of the tunable light. A signal processor responsive to the electrical detection signal interprets a shift in the wavelength of the magnitude minimum or maximum due to the environmental stimulus calculated from the recorded electrical detection signals, and provides a signal indicative of said stimulus.

In accordance with a further illustrative non-limiting implementation, the said optical sensors are of the reflective Bragg grating type. The sensors reflect light, having maxima or minima inside the maxima at different or the same reflection wavelength for each sensor, said sensors varying their spectral positions due to an environmental stimulus, such as strain, pressure, temperature, electrical current or magnetic field imposed thereon.

In accordance with a further exemplary non-limiting illustrative implementation, the said optical sensors are of the transmission Bragg grating type. The sensors transmit light, having minima or maxima inside the minima at a different or the same transmission wavelength for each sensor, said sensors varying their spectral positions due to an environmental stimulus, such as strain, pressure, temperature, electrical current or magnetic field imposed thereon.

In accordance with a further exemplary illustrative non-limiting implementation, the said optical sensors are of reflective etalon type. The sensors reflect light, having maxima, minima or maxima and minima at a different reflection wavelength for each sensor, said sensors varying their spectral positions due to an environmental stimulus, such as strain, pressure, temperature, electrical current or magnetic field imposed thereon.

In accordance with a further exemplary illustrative non-limiting implementation, the said optical sensors are of transmission etalon type. The sensors transmit light, having maxima, minima or maxima and minima at a different transmission wavelength for each sensor, said sensors varying their spectral positions due to an environmental stimulus, such as strain, pressure, temperature, current or magnetic field imposed thereon.

The illustrative non-limiting exemplary implementations described herein provide low cost, workable, practical diagnostic systems which function in cooperation with remote optical fiber sensor systems to measure static and dynamic strain, pressure, temperature, electrical currents and magnetic fields as well as acoustic or vibratory perturbations of items or structures and chemical and biological parameters. The remote sensors may be disposed on structures made of metal, plastic, composite, or any other materials that expand, contract, or vibrate, or the sensors may be embedded within such structures or immersed in liquids or gasses. The implementations also provide a wavelength-tunable VCSEL, tunable smoothly and monotonically, and in particular, linearly or sinusoidally tunable with time. The implementations further provide individual illumination of each sensor, thereby allowing all the tunable VCSEL power to be resident in a single narrow wavelength band at any instant in time. Ultra-fine tuning of tunable VCSELs to a few parts per million will allow another order of magnitude increase in precision due to higher resolution and improved computational methods and statistical processing. The very low mass of the MEMS tuning mechanisms allow very high tuning speeds with very low hysteresis, providing the ability to average out optical noise in the sensor systems with many data points and allowing very close spacing of data in wavelength.

BRIEF DESCRIPTION OF THE DRAWINGS

These and other exemplary illustrative non-limiting features and advantages will be better and more completely understood by referring to the following detailed description in conjunction with the drawings, of which:

FIGS. 6A–6C show exemplary numerically-calculated plots; and

FIGS. 7A–7F show an additional series of illustrative exemplary non-limiting graphs of time-varying tuning control signals applied to a tunable VCSEL with resulting time variations of the spectral position of emitted light.

DETAILED DESCRIPTION OF EXEMPLARY ILLUSTRATIVE NON-LIMITING IMPLEMENTATIONS

Figure 1:
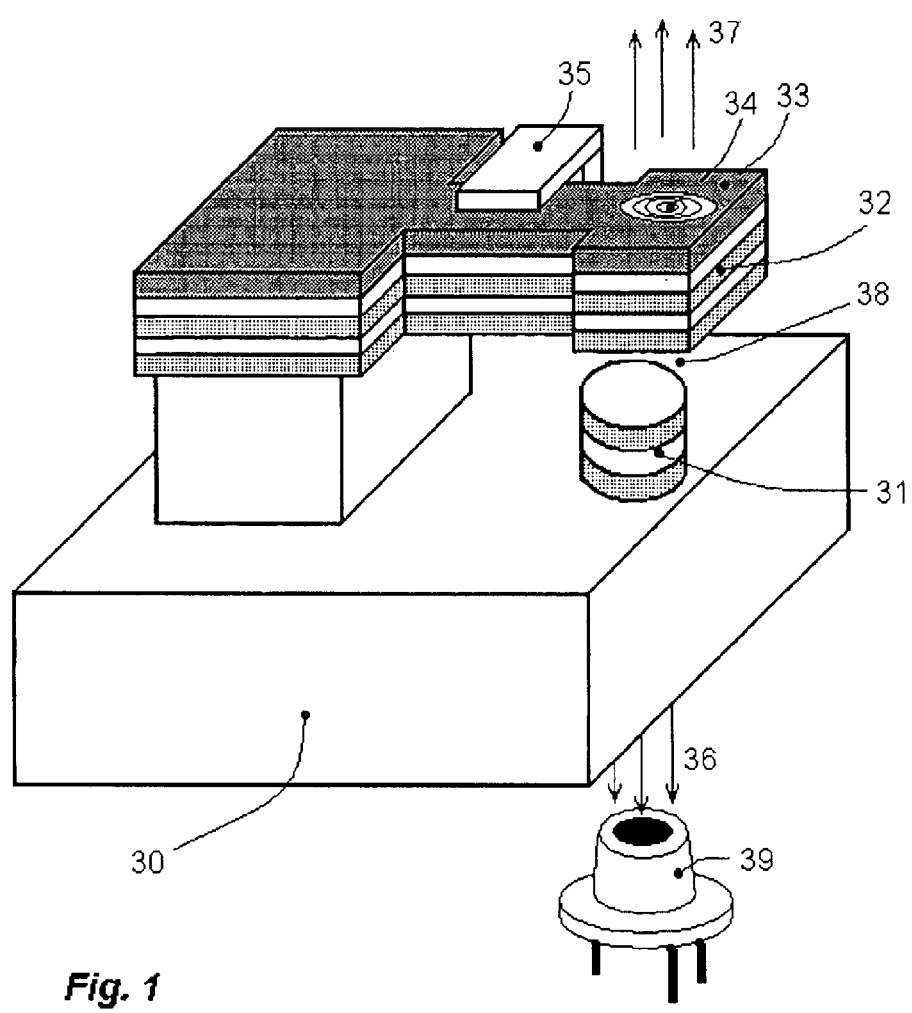
FIG. 1 is a schematic illustration of a non-limiting exemplary illustrative VCSEL incorporating one example of an integrated MEMS (micro-electromechanical machine system)

FIG. 1 is an illustrative schematic drawing of an exemplary illustrative VCSEL incorporating one non-limiting example of an integrated MEMS (micro-electromechanical machined system) tuning mechanism in the form of a cantilevered mirror and optional lens. Substrate chip 30 has fabricated upon it, when in wafer form, a multilayer stack of materials forming the light emitting VCSEL 31 and tuning components. Exemplary tuning components may consist of a mirror stack 32, an actuator and structural means 33 that change the tuning cavity length 38, a diffractive optical lens 34 (optional), and a capacitive cantilever position monitor 35 (optional). Light beams may be emitted in directions 36 and/or 37. If either mirror 32 or bottom of stack 31 is opaque, light is emitted only in one direction 37 or 36 respectively. Emission in both directions is possible if both 32 and 31 are partially transparent. This arrangement provides a simple means for optical power monitoring with a photodiode 39 for the purpose of spectral power uniformity control. Electrical connections are not shown for simplicity.

Figure 2A:
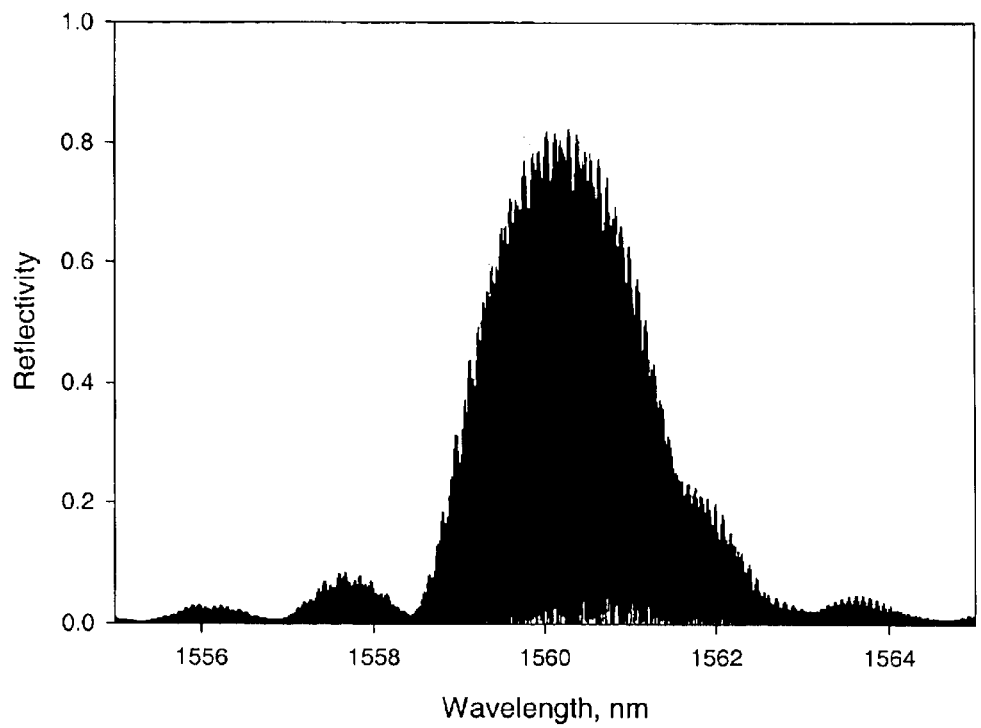
FIG. 2A shows a prior art illustrative numerically calculated reflection spectrum.
Figure 2B:
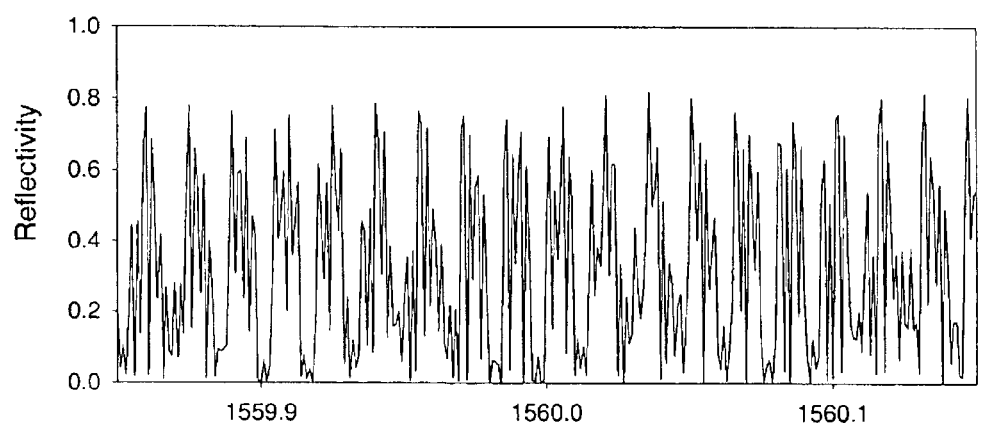
FIG. 2B shows a magnified portion of the prior art reflection spectrum shown in FIG. 2A.

FIG. 2A is an illustrative numerically calculated reflection spectra from a prior art sensor array consisting of 5 FBGs with peak Bragg wavelength of 1560 nm and one FBG with peak Bragg wavelength of 1561 nm spaced 5 cm apart. FIG. 2B is a magnified portion of the reflection spectra for the illustrative example of FIG. 2A.

Figure 3A:
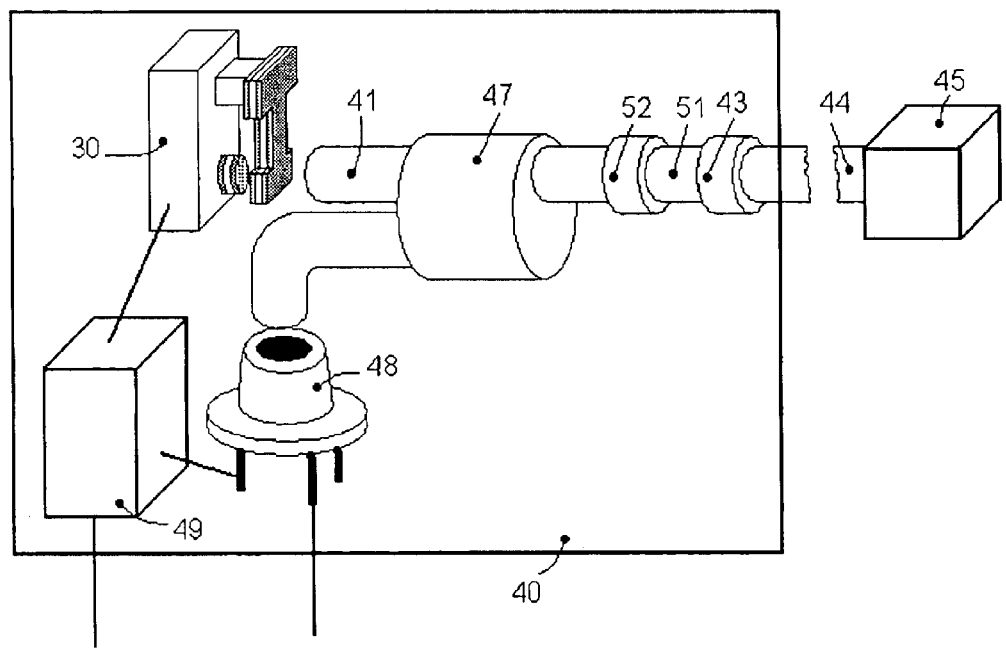
FIGS. 3A–3D show example non-limiting illustrative portions of the FIG. 3A sensor diagnostic system using different reference fiber arrangements.

FIG. 3A is a schematic block diagram of a first illustrative, exemplary non-limiting sensor diagnostic system capable of determining the value of static and dynamic physical stimuli in a reflection mode employing a tunable VCSEL as an optical excitation source and a photodiode or similar simple device as a detector. In said illustrative example, a tunable VCSEL 30 is assembled with necessary means to fiber couple 41 the emitted light, and couple the VCSEL assembly 40 to an external fiber 44 to convey the laser light to an optical sensor or sensor array 45 in a reflection mode and to a reference fiber length 51 (serving as a arm of an interferometer) disposed between said VCSEL assembly and an optical sensor or sensor array 45. One or two reflection means (43 and 52) may be disposed in a reference fiber length to create a reference optical length in a fiber 51. A coupler or circulator 47 is provided to divert the optical signal reflected from the sensor 45 and the reflection means (43 or 43 and 52) to the photodetector 48, the electrical signal from which is relayed to the control block circuitry 49 and external electronic circuitry as required. A circulator also provides the function of isolating the VCSEL from back-reflected light. If a coupler is used to divert the light to the detector, a separate isolator may be incorporated between it and the laser. The control block 49 may or may not control the laser temperature via a thermoelectric element or other means and may or may not adjust the laser power output according to a signal from a monitor photodiode 39, as required.

Figure 3B:
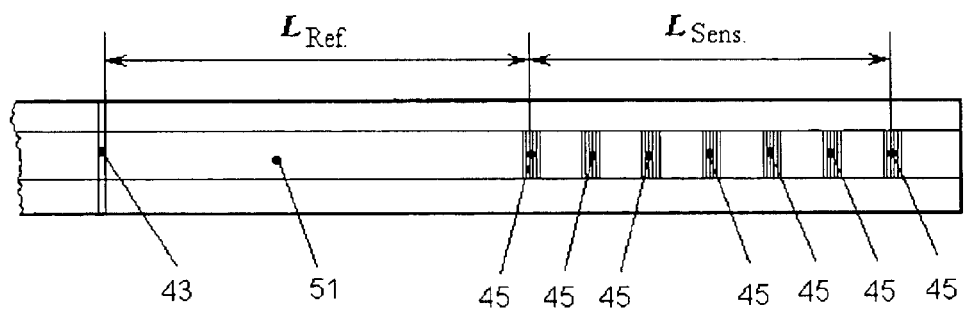

In more detail, the FIG. 3A diagnostic system 40 includes a MEMS-tunable VCSEL 30, a fiber light coupling means 41, an optical circulator (or an isolator plus a coupler) 47, a reference fiber length 51 defined by one (52) or two (52 and 43) reflective means, exterior fiber 44 and coupling means to the sensor or sensor array 45, a photodetector 48, and a control block 49. In this implementation, the MEMS-tunable VCSEL 30 provides a wavelength-tunable light in response to a tuner control signal provided by control block 49. This tunable light provided by tunable VCSEL 30 is launched into an optical waveguide 44 such as an optical fiber. A sensor or sensor array 45, in this implementation a Bragg grating sensor array (schematically shown in FIG. 3B), providing at least one optical sensor, is disposed in the path of the tunable light. FIG. 3B shows example non-limiting part of a sensor diagnostic system of FIG. 3a consisting of the reference fiber length defined by a single reflective means 43 and the first sensing element of a sensor array 45 in the form of the FBG and the fiber optic sensor array 45 in the form of a number of a FBGs distributed along some length having the same or different Bragg wavelengths. The sensor array 45 includes individual Bragg gratings that each reflects light having different or the same associated amplitude reflection maxima at individual or common reflection wavelengths. In the exemplary implementation, the wavelength position of the amplitude maximum reflected by each of the Bragg gratings in the array 45 varies in response to a physical stimulus or perturbation imposed 6n the corresponding sensor.

The MEMS-tunable VCSEL 30, by continuously scanning its output spectrum, individually illuminates each of the sensors in turn within the sensor array 45 in a wavelength band including the wavelength of maximum or minimum reflection associated with each sensor. An optical isolation and directing device such as optical circulator 47 is disposed in the path of the tunable light between the tunable VCSEL 30 and the sensor array 45. An optical isolation and directing device efficiently isolates the tunable VCSEL from light reflected by the sensor array 45 or from the reflectors disposed in the reference path and diverts the reflected signals to a simple and inexpensive optical detector 48, such as a photodiode, disposed in the path of the light. The detector 48 provides an electrical detection signal indicative of the power of the reflected light that is directly related to the wavelength by means of the tuning control signal and the wavelength reference, if said wavelength reference is utilized. The series of optical signals obtained during a scanning cycle can contain one or more absorption or reflection bands from one or more wavelength reference devices that can be incorporated for additional wavelength accuracy. Said reference signals do not change in wavelength position with any of the external stimuli measured by the sensors, and can be related in time to the tuning control signal.

Control block 49 responds to the electrical detection signal from the photodetector 48 in the example implementation by calibrating a variable voltage or other tuning signal for the tunable VCSEL 30 to the wavelengths of the wavelength references, and by providing said tuning signal to said VCSEL. Control block 49 may also include a signal processor responsive to the electrical detection signal for detecting a shift in the wavelength of maximum reflection on each of the sensors due to physical stimuli, and/or may cooperate with external circuitry to provide a signal indicative of the stimuli for each of the sensors in units commonly accepted for a specific stimulus. More detail on the signal processing will be given below. Control block 49 may also control the laser temperature by any of several known means and adjust the laser power to provide a constant power output with respect to wavelength using an independent monitor detector 39 (FIG. 1).

In still more detail, referring to FIG. 3A, diagnostic system 40 may include a MEMS-tunable VCSEL 30 that in this implementation (FIG. 1) has a rear reflector stack of alternating quarter-wave layers of two different materials 31, the Fabry-Perot cavity region that contains the active material 31 (here a solid optical cavity), and an upper reflector 32, made as movable, suspended mirror layers with different indices of refraction of transparent material on a cantilever as illustrated, or, alternately, as a reflective or partially reflective single layer, such as aluminum. The relative position of the movable mirror structure with respect to the rest of the structure is changeable by the application of an electrostatic field or other control force, forming a variable optical cavity 38 (here an air or vacuum optical cavity). The mirror structure could be made in a form of a diaphragm suspended by other means by selective etching and release techniques, the relative position of which with respect to the rest of the structure is also changeable by the application of an electrostatic force, magnetic force or other force. The result of this is that the effective optical distance between the two reflectors making up the cavity 38 is adjustable. Since the resonant wavelength depends on this distance, the characteristic wavelength of the tunable VCSEL is continually tuned, for example, by varying the applied voltage and thereby the electrostatic field between the upper reflector and the remainder of the device.

It is desirable to provide energy within the tunable VCSEL 30 to achieve lasing. It should be noted that the energy could be provided by optical pumping means or by electrical pumping means (p-n or p-i-n junction). Although both methods are suitable for a sensor system, the electrically pumped implementation is preferred from the point of view of lowest cost and greatest simplicity.

The operating wavelengths of the tunable VCSEL can be in the communication wavelength band (Chang-Hasnain [IEEE J. on Select. Topics in Quantum Electronics, V 6, N 6, November 2000, p. 978] Vkhshoori [Electronics Letters, may 1999, V. 35, N. 11 p. 900]) or around 960 nm (J. S. Harris, [Appl. Phys. Lett. 68 (7), February 1996 p. 891]) or in any other desired band in which VCSELs are produced. When the distance between the tunable VCSEL 30 and a Bragg grating or other type of sensor 45 does not exceed about 1 km, many wavelength bands are usable. When this distance exceeds about 1 km, the losses may become too high at wavelengths not in the communications bands around 1310 nm and 1550 nm and tunable VCSELs 30 emitting within the communication wavelength bands may be more suitable.

A current control circuit within control block 49 (FIG. 2) provides an electrical current to the tunable VCSEL 30, which controls the intensity of the output light. Adjusting the current through the diode (VCSEL active area 31) also causes slight changes in wavelength, hence it is undesirable in this case. In addition, a temperature control circuit could be used in the illustrative implementation to provide a current drive to a thermoelectric (TE) cooler to stabilize the temperature of the tunable VCSEL 30 if needed. Other devices may be used to control the temperature if desired. A voltage control circuit can be used to control the electrostatic force between the movable reflector 32 and the active layers of the tunable VCSEL 31 and, by such means, can control the wavelength emitted by the tunable VCSEL in the illustrative implementation. It should be noted that other control mechanisms than electrostatic can be used to position the VCSEL tuning mirror, and the tuning signal may or many not be a voltage.

In all exemplary implementations, the tunable VCSEL 30 can provide a divergent output light beam to either the end plane of fiber 41, placed in close vicinity to the tunable VCSEL and perpendicular to the direction of emitted light propagation (butt-coupling method) or to a focusing lens, also represented by element 41, that provides focused light to optical fiber. The lens may instead be a lens system that provides this function. The lens also could be realized as a diffractive element 34 written photolithographically on the surface of the VCSEL mirror, adjacent to the fiber 41 or on the backside of the chip in the path of the light beam 36.

It should be noted that an optical isolator and a wavelength-independent two-way splitter, placed in line, might replace the optical circulator 47. This approach is less costly, although a significant part of the optical power will be lost going each way.

In the exemplary FIG. 3A implementation, the light from the tunable VCSEL 30 propagates toward the sensor 45 that is composed of an array of sensors disposed at intervals along the optical fiber 44. Each Bragg grating sensor within sensor array 45 reflects a predetermined narrow wavelength band of light and passes the remaining light on toward the next sensor. If said predetermined reflected narrow wavelength bands of said sensors comprising sensor array 45 are overlapping and if the intervals between said sensors are less or comparable to the coherence length of said tunable VCSEL (which may be 2 meters or longer), the resultant reflection spectrum of the sensor array will have a complex shape as shown in FIG. 2, so the amplitude features of each sensor cannot be distinguished directly. However, according to an exemplary illustrative non-limiting implementation, if the light reflected from such a sensor array 45 is mixed with the light reflected from the reference fiber length 51 to cause them to interfere with each other (which is possible when the difference between the length of 51 and the distance between the first and the last sensor does not exceed the coherence length of the tunable VCSEL 30), the contributions of each sensor to the reflectivity spectra and through that the particular value of the physical stimuli at the position of each sensor may be determined through the special signal processing algorithm. Said signal processing algorithm includes the discrete Fourier Transform of the recorded spectrum.

Figure 3C:
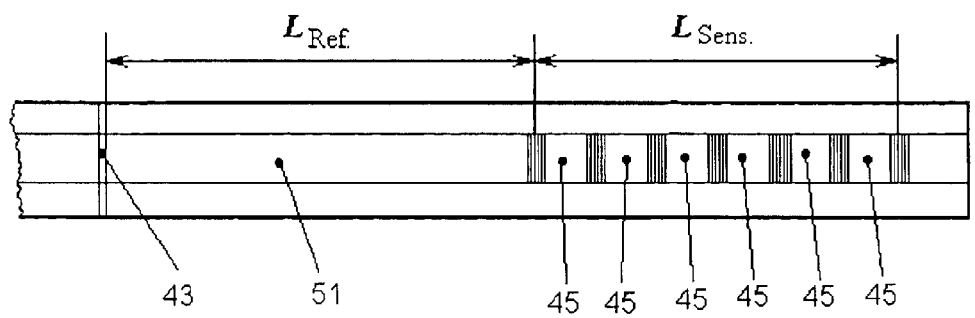
Figure 3D:
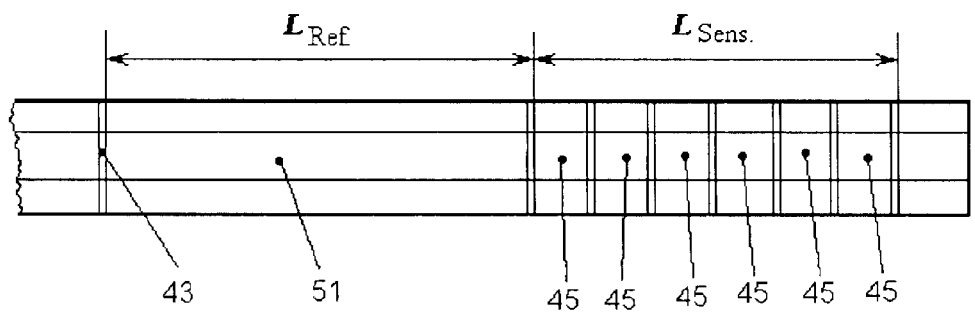
Figure 4A:
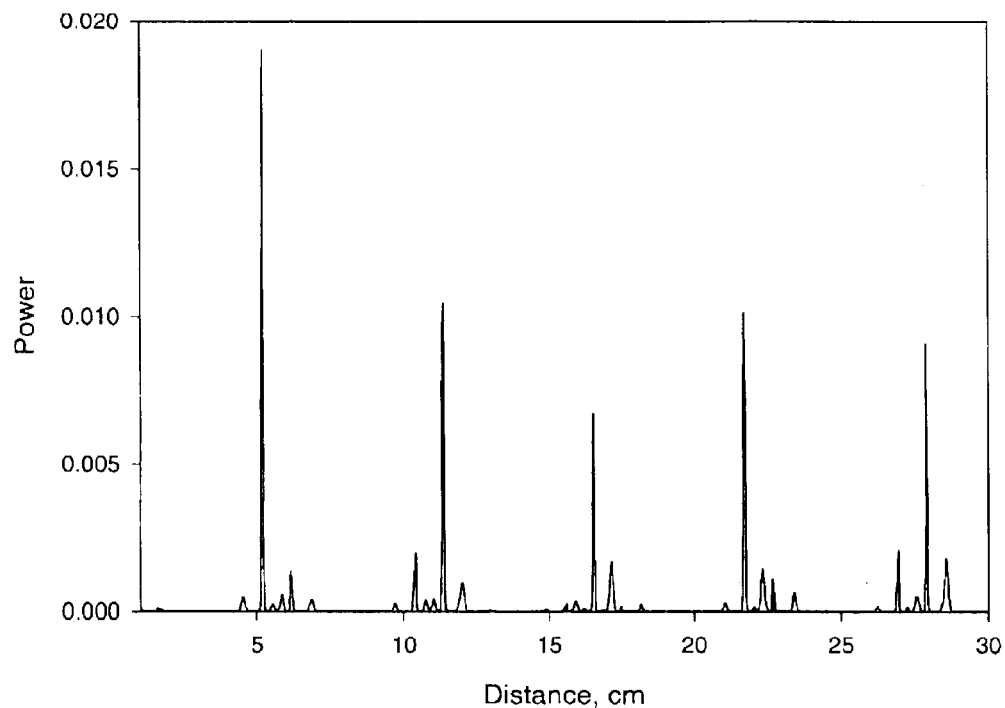
FIGS. 4A and 4B show exemplary numerically-calculated Fourier transform plots.

The numerically calculated example discrete Fourier Transform of the implementation as in FIG. 3B when interrogating the sensor array consisting of 5 FBGs with peak Bragg wavelength of 1560 nm is given in FIG. 4A—an exemplary plot of numerically calculated Fourier transform of a reflection spectrum such as obtained in a diagnostic system of FIG. 3*a* when interrogating the sensor array consisting of 5 FBGs with peak Bragg wavelength of 1560 nm. One can see that the coefficients corresponding to each of the sensors of the sensor array 45 are clearly separated in a spatial domain waveform. The peaks corresponding to each of the sensors on a spatial domain waveform obtained by the discrete Fourier Transform of the recorded spectrum can give accurate information on the spacing between FBGs comprising the sensor array. Hence, an etalon-like sensor array such as shown in FIGS. 3C and 3D can be interrogated by the sensor diagnostic system of the exemplary illustrative non-limiting implementation.

Figure 4B:
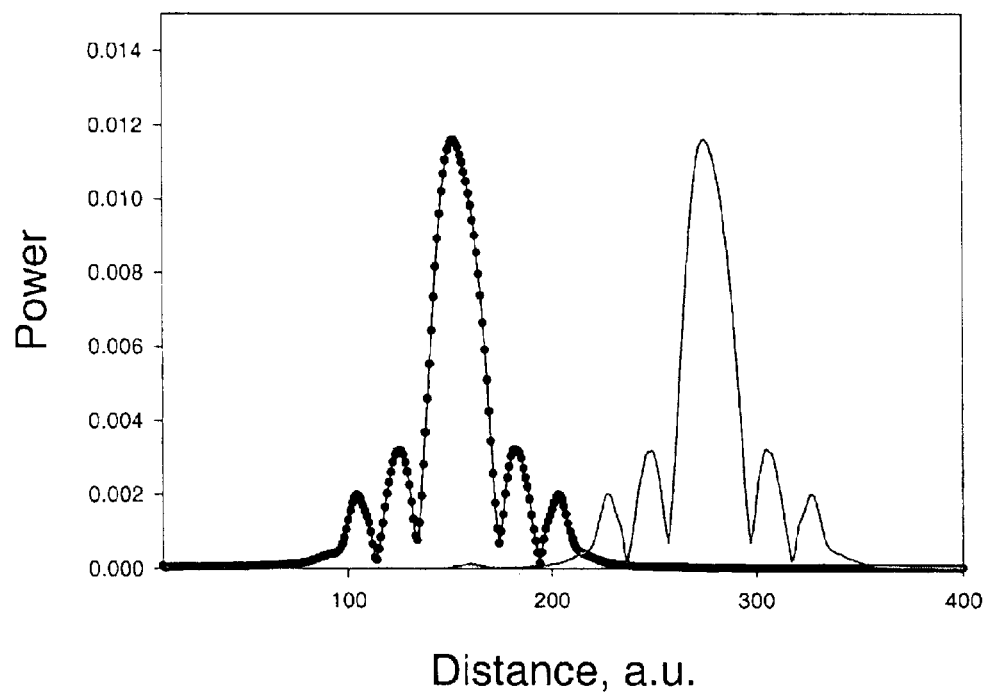

As an illustrative example, FIG. 4B gives an exemplary plot of a part of numerically calculated Fourier transforms of a reflection spectra such as obtained in a diagnostic system of FIG. 3A. FIG. 4B shows an exemplary plot of a part of numerically calculated Fourier transforms of a reflection spectra such as obtained in a diagnostic system of FIG. 3a when interrogating the sensor array consisting of 5 FBGs with peak Bragg wavelength of 1560 nm for two different positions of one of the FBGs. (Note: FIGS. 4A–4B show interrogation of the sensor array consisting of 5 FBGs with a peak Bragg wavelength of 1560 nm for two different positions of one of the FBGs caused by the applied physical stimuli, such as, for a nonlimiting illustrative example, strain).

As mentioned above, it is possible to interrogate sensor arrays by applying mathematical analysis to the discrete Fourier Transform of the recorded spectrum. However, the resolution, accuracy and dynamic range of the diagnostic system of an exemplary illustrative implementation can be significantly improved by applying filtering to the data array obtained by performing discrete Fourier Transform of the recorded spectrum and then by performing the inverse discrete Fourier Transform of the filtered array. For a non-limiting illustrative example, separate data arrays (one array per each sensor) may be generated by performing the inverse discrete Fourier Transform on each array. This may be accomplished for each array by setting to zero all coefficients except for those around the peak in the discrete Fourier Transform spectrum corresponding to this particular sensor array. By performing such a mathematical operation, the number of spectra containing the reflection feature of each sensor alone (without interference from the other sensors in the array, as in FIG. 2). Other methods of filtering of the Fourier Transformed data may be applied as well. After the reconstructed reflection spectra of the gratings are obtained, additional mathematical processing may be performed to increase the accuracy and resolution of said sensor diagnostic system. For a non-limiting illustrative example of the FBG sensor, the particular value of the physical stimulus in the location of each sensor can be determined from the wavelength position of the reflection peak. In this case, the spectrum of said sensor reconstructed according to the abovedisclosed reflection algorithm might be, for example, interpolated by fitting to some predetermined function (through, for example, the Newton- Raphson method or by any other fitting method known to those skilled in the art). The wavelength position of the reflection peak (and through that the particular value of the physical stimuli at the location of this particular sensor) will be in this case unambiguously determined from the fitted function. Other methods may be used for these purposes as well.

To increase the number of sensors interrogated by the same instrument, in addition to the multiplexing technique disclosed above (i.e., that known as Optical Frequency Domain Multiplexing, or OFDM), the sensors in array 45 in the illustrative implementation, can be modified slightly and the several similar but modified arrays can be placed in parallel or in series and in turn multiplexed by Wavelength Division Multiplexing (WDM). Such a modification may be applied to all the sensors in each wavelength division multiplexed array. Thus, WDM of a series of sensor arrays is realized by sensors 45 having different central reflection wavelengths. In this implementation, the sensors can be fiber Bragg gratings, planar Bragg gratings or Fabry-Perot etalon sensors.

FIG. 3C shows example non-limiting part of a sensor diagnostic system of FIG. 3a consisting of the reference fiber length defined by a single reflective means 43 and the first part of the first sensing element of a sensor array 45 in the form of the FBG and the fiber optic sensor array 45 in the form of a number of Fabry-Perot cavities distributed along some length of the fiber defined by the pairs of FBGs having substantially the same Bragg wavelengths.

FIG. 3D shows example non-limiting part of a sensor diagnostic system of FIG. 3a consisting of the reference fiber length defined by a single reflective means 43 and the first reflector of the first sensing element of a sensor array 45 and the fiber optic sensor array 45 in the form of a number of Fabry-Perot cavities distributed along some length of the fiber defined by the pairs of reflectors.

Figure 5A:
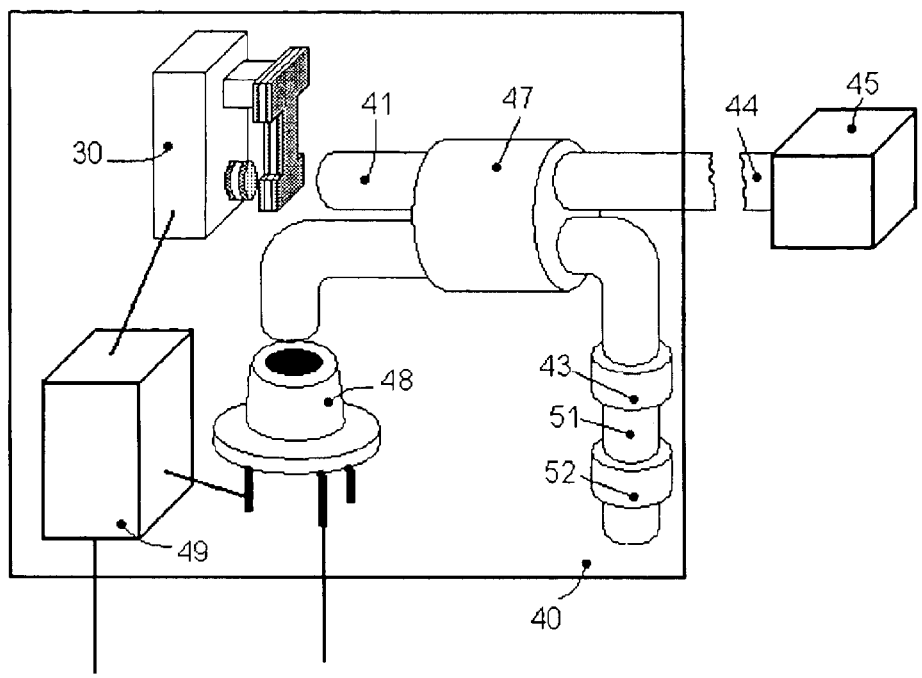
FIGS. 5A–5F show additional exemplary non-limiting illustrative sensor diagnostic system implementations.

FIG. 5A is a schematic block diagram of a second illustrative, exemplary non-limiting sensor diagnostic system capable of determining the value of static and dynamic physical stimuli in a reflection mode employing a MEMS-tunable VCSEL as an optical excitation source and a photodiode or similar simple device as a detector. In said illustrative example, a tunable VCSEL 30 is assembled with necessary means to fiber couple 41 the emitted light. A splitter in the form of 2×2 coupler 47 may be provided to divide the tunable light into two separate optical paths. One path delivers the light emitted by VCSEL to an optical sensor or sensor array 45 in a reflection mode and the other delivers light to the reference path. One or two reflection means (43 and 52) may be disposed in the reference path to create a reference optical length in a fiber 51. Light back reflected by 43 and 52 is then diverted by the coupler 47 to the photodetector 48. Light reflected from at least one sensor element in sensor array 45 is also diverted by the coupler 47 to the photodetector 48 and mixed by said coupler with the light reflected from the reference path to create optical interference-caused beating in the electrical signal from photodetector 48, which is transferred to the control block circuitry 49 and external electronic circuitry as required. The control block 49 may or may not control the laser temperature via a thermoelectric element or other means and may or may not adjust the laser power output according to a signal from a monitor photodiode 39, as required. A separate isolator may be required between the VCSEL 30 and the coupler 47 to isolate the VCSEL from back-reflected light.

In more detail, the FIG. 5A exemplary illustrative diagnostic system 40 includes a MEMS-tunable VCSEL 30, a fiber light coupling means 41, an optical coupler 47 (which may be, in a nonlimiting example, a 2×2 coupler), an optical isolator disposed between said tunable VCSEL and optical coupler, exterior fiber 44 and coupling means to the sensor or sensor array 45, a reference fiber length 51 defined by two reflective means (52 and 43) disposed in a reference path that is separate from the path connecting the tunable VCSEL and sensor array, a photodetector 48, and a control block 49. The difference between the first and second aspects of the first exemplary non-limiting implementation is that in the second aspect the reference path is physically separate from the sensing path. Such a diagnostic system is slightly more complex, but can provide better isolation of the reference path from the physical stimuli imposed on the sensor array, thus should be more accurate.

Figure 5B:
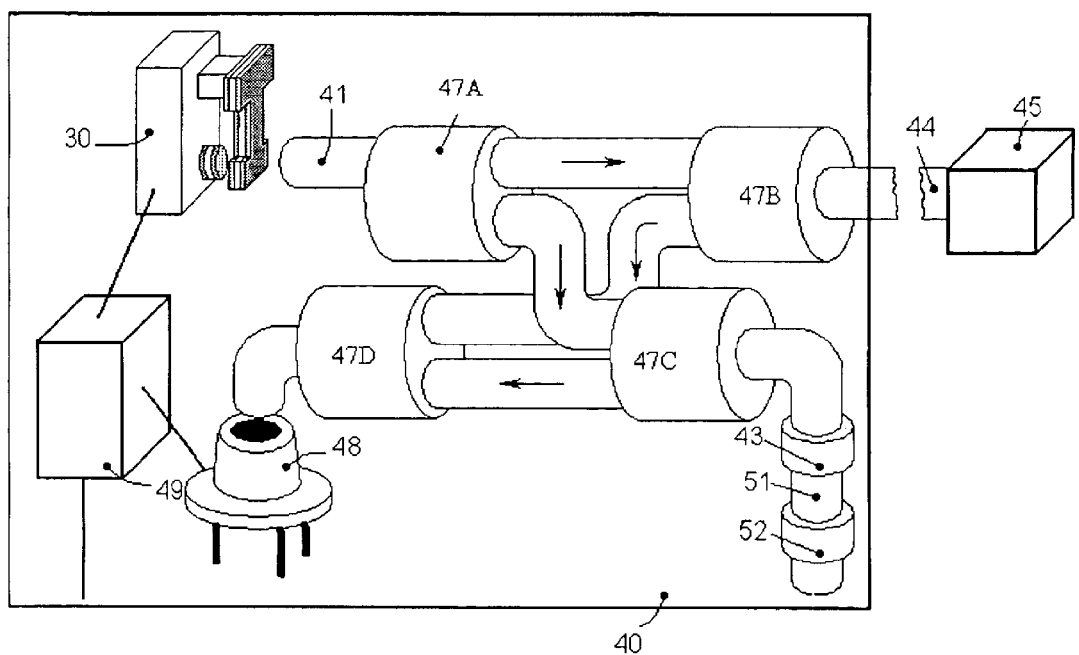

Instead of using a single coupler 47 as in FIG. 5A, four 1×2 couplers may be used as schematically shown in FIG. 5B. FIG. 5B is a schematic block diagram of a third illustrative, exemplary sensor diagnostic system capable of determining the value of static and dynamic physical stimuli in a reflection mode employing a MEMS-tunable VCSEL as an optical excitation source and a photodiode or similar simple device as a detector. In said illustrative example, a tunable VCSEL 30 is assembled with necessary means to fiber couple 41 the emitted light. A splitter (or divider) in the form of 1×2 coupler 47A may be provided to divide the tunable light into two separate optical paths. One path delivers the light emitted by the VCSEL to the sensor or sensor array 45 through another splitting means 47B (which may be 2×1 optical coupler or optical circulator) and a second path delivers light emitted by the VCSEL to the reference path through another splitting means 47C (which may be 2×1 optical coupler or optical circulator). One or two reflection means (43 and 52) may be disposed in a reference path to create a reference optical length in a fiber 51. Light back reflected by 43 and 52 is then diverted by the coupler 47D to the photodetector 48. Light reflected from at least one sensor element in sensor array 45 is also diverted by the coupler or circulator 47B and coupler 47D to the photodetector 48 and mixed by coupler 47D to create optical interference-caused beating in the electrical signal from photodetector 48, which is transferred to the control block circuitry 49 and external electronic circuitry as required. The control block 49 may or may not control the laser temperature via a thermoelectric element or other means and may or may not adjust the laser power output according to a signal from a monitor photodiode 39, as required.

Other modifications of the sensor diagnostic system of this aspect of the non-limiting exemplary implementation, which may be implemented within the skills of the present state of the art, are also within the scope of exemplary non-limiting illustrative implementations. Other aspects of this implementation are the same as in the first aspect of the first implementation, as drawn in FIG. 3A. In this implementation, the sensors can be fiber Bragg gratings, planar Bragg gratings or Fabry-Perot etalon sensors.

Figure 5C:
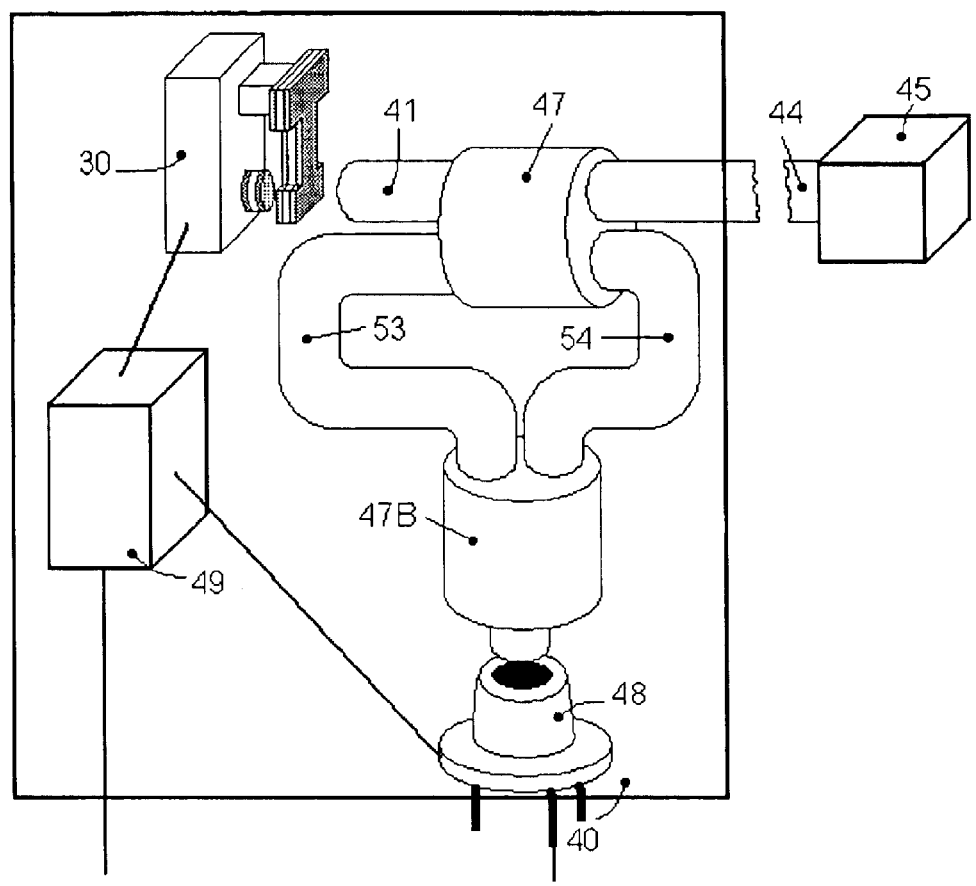

FIG. 5C is a schematic block diagram of a fourth illustrative, exemplary sensor diagnostic system capable of determining the value of static and dynamic physical stimuli in a reflection mode employing a MEMS-tunable VCSEL as an optical excitation source and a photodiode or similar simple device as a detector. In said illustrative example, a tunable VCSEL 30 is assembled with necessary means to fiber couple 41 the emitted light. A splitter in the form of 2×2 coupler 47 may be provided to divide the tunable light into two separate optical paths. One path is deliver the light emitted by VCSEL to the sensor or sensor array 45 and another path to deliver light emitted by VCSEL to the reference path in the form of one arm of interferometer 54. Light reflected from at least one sensor element in sensor array 45 is diverted by the coupler 47 to another arm of said interferometer 53. Light waves from both arms of the interferometer are mixed with each other to create optical interference-caused beating in the electrical signal from photodetector 48, and then directed to the photodetector 48 which is transferred to the control block circuitry 49 and external electronic circuitry as required. The control block 49 may or may not control the laser temperature via a thermoelectric element or other means and may or may not adjust the laser power output according to a signal from a monitor photodiode 39, as required.

In more detail, the FIG. 5C example illustrative implementation of a diagnostic system 40 includes a MEMS-tunable VCSEL 30, a fiber light coupling means 41, an optical coupler 47 (which may be, for nonlimiting example, a 2×2 coupler), an optical isolator disposed between said tunable VCSEL and optical coupler, exterior fiber 44 and coupling means to the sensor or sensor array 45, an interferometer, having two arms, one of which is a "reference" arm 54 and another is a "signal" arm 53, a photodetector 48, and a control block 49. In this non-limiting exemplary implementation, no reflecting means on the reference path is needed.

Figure 5D:
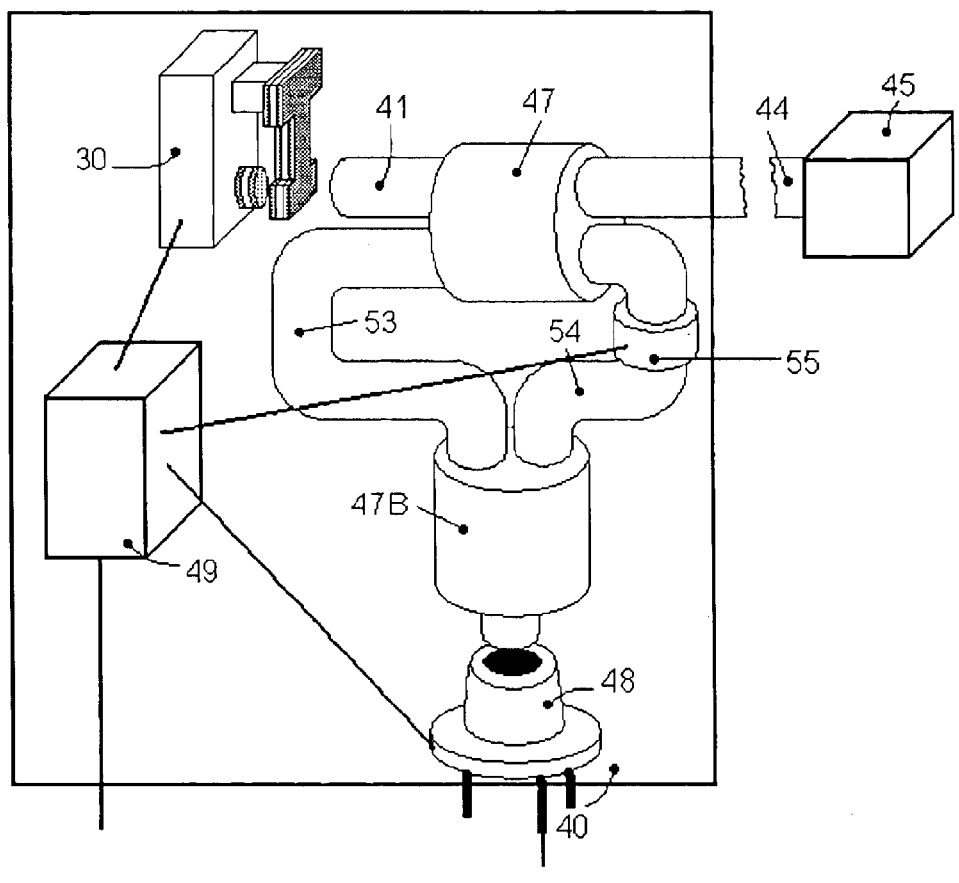

FIG. 5D is a schematic block diagram of a fifth illustrative, exemplary sensor diagnostic system capable of determining the value of static and dynamic physical stimuli in a reflection mode employing a MEMS-tunable VCSEL as an optical excitation source and a photodiode or similar simple device as a detector. In said illustrative example, a tunable VCSEL 30 is assembled with necessary means to fiber couple 41 the emitted light. A splitter in the form of a 2×2 coupler 47 may be provided to divide the tunable light into two separate optical paths. One path delivers the light emitted by the VCSEL to the sensor or sensor array 45 and another path delivers light emitted by the VCSEL to the reference path in the form of one arm of interferometer 54. Light reflected from at least one sensor element in sensor array 45 is diverted by the coupler 47 to another arm of said interferometer 53. Light waves from both arms of the interferometer are mixed with each other to create the interference-caused beating in the electrical signal from photodetector 48 and then directed to the photodetector 48, which is transferred to the control block circuitry 49 and external electronic circuitry as required. The control block 49 may or may not control the laser temperature via a thermoelectric element or other means and may or may not adjust the laser power output according to a signal from a monitor photodiode 39, as required. A tunable time delay element or frequency shifting element 55 is disposed in one of the arms of said interferometer to enlarge the detection range of the instrument.

Referring now to FIG. 5D, to interrogate sensor arrays with an array length significantly exceeding the coherence length of the tunable VCSEL, the tunable time delay element 55 may be disposed on the reference arm of the interferometer in order to match the sensing path and reference path to within the coherence length of the tunable VCSEL. Frequency shifting means may be disposed instead of the tunable time delay means. Other aspects of this implementation are the same as in the first aspect of the first non-limiting illustrative implementation, as drawn in FIG. 3A. In this implementation, the sensors can be fiber Bragg gratings, planar Bragg gratings or Fabry-Perot etalon sensors.

Figure 5E:
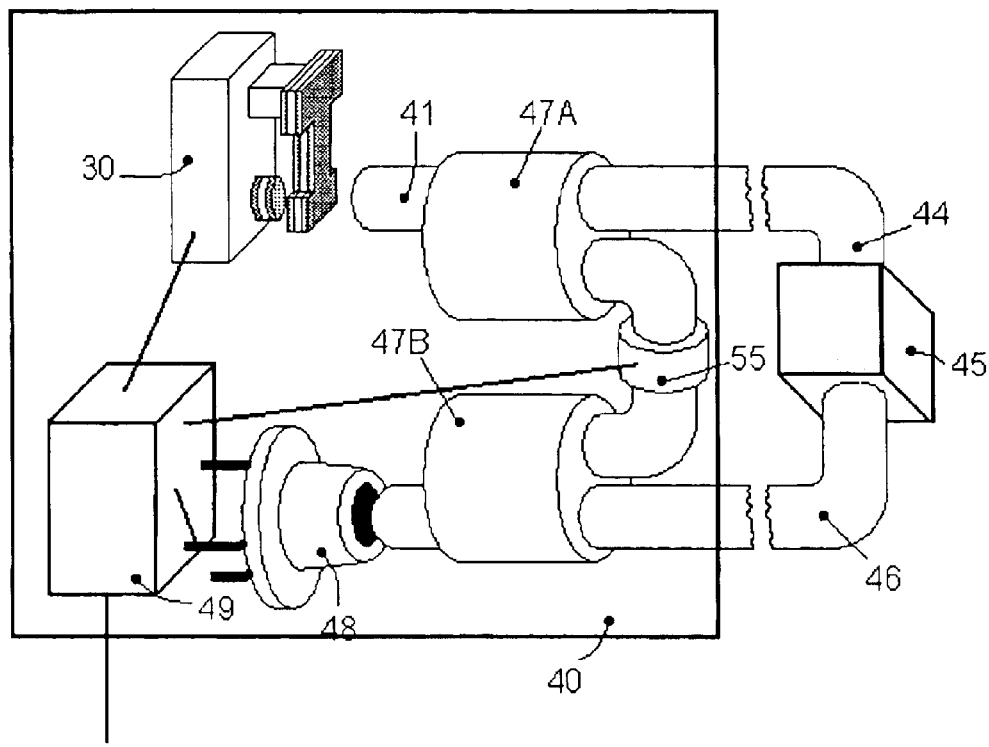

FIG. 5E is a schematic block diagram of a further illustrative, exemplary sensor diagnostic system—this one capable of determining the value of static and dynamic physical stimuli in a transmission mode employing a tunable VCSEL as an optical excitation source and a photodiode or similar simple device as a detector. In said illustrative example, a tunable VCSEL 30 is assembled with necessary means to fiber couple 41 the emitted light. A splitter in the form of 1×2 coupler 47A may be provided to divide the tunable light into two separate optical paths. One path delivers at least some of the light emitted by VCSEL to the sensor or sensor array 45 and another path delivers at least some of the light emitted by the VCSEL to the reference path. Light transmitted through the sensor array 45 is combined by the 2×1 coupler 47B with the light transmitted through the reference path. Mixed light waves are mixed with each other to create optical interference-caused beating in the electrical signal from photodetector 48 and then directed to the photodetector 48, which is transferred to the control block circuitry 49 and external electronic circuitry as required. The control block 49 may or may not control the laser temperature via a thermoelectric element or other means and may or may not adjust the laser power output according to a signal from a monitor photodiode 39, as required. A tunable time delay element or frequency shifting element 55 may be disposed in the reference path to enlarge the detection range of an instrument.

In the FIG. 5E exemplary illustrative implementation diagnostic system 40 includes a MEMS-tunable VCSEL 30, a fiber light coupling means 41, an optical divider 47A (which may be, as a nonlimiting example, a 1×2 coupler), an optical isolator disposed between said tunable VCSEL and optical coupler, exterior fiber 44 and coupling means to the sensor or sensor array 45, exit fiber 46, a reference path (i.e., the reference arm of the interferometer), an optical combiner 47B (which may be, as a non-limiting example, a 2×1 coupler), a photodetector 48, and a control block 49.

In this exemplary implementation, the sensor array 45 includes individual Bragg gratings that each transmit light having different, non-overlapping, associated amplitude transmission minima at individual transmission wavelengths. In the exemplary implementation, the wavelength position of the amplitude minimum transmitted by each of the Bragg gratings in the array 45 varies in response to a physical stimulus or perturbation imposed on the corresponding sensor. Other aspects of this implementation are the same as in the first implementation, as drawn in FIGS. 3A and 5A–D.

Figure 5F:
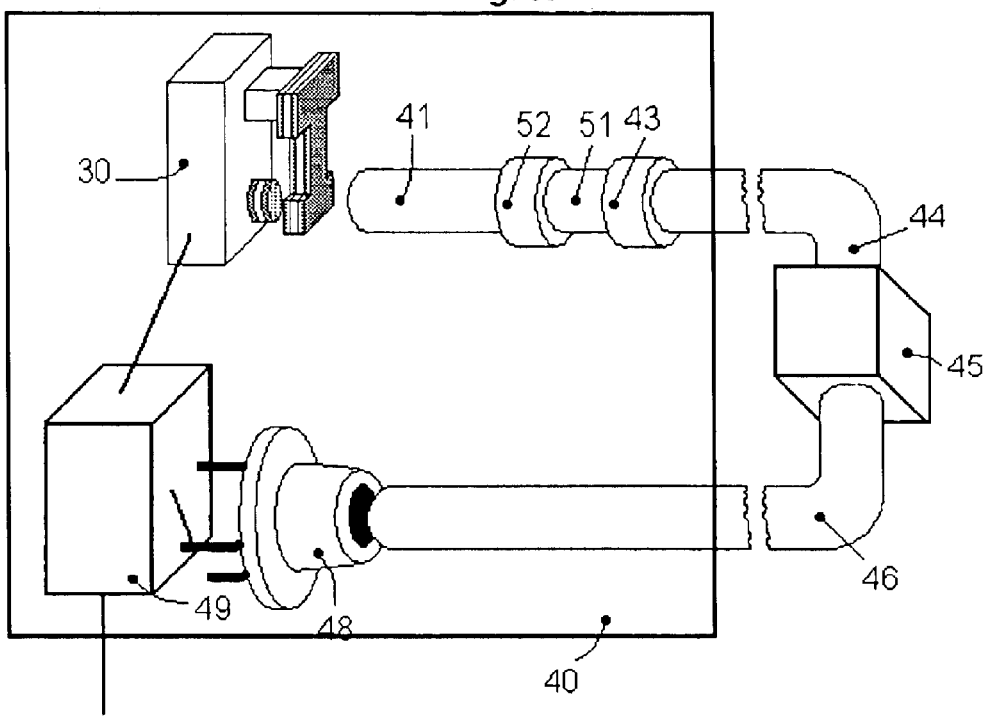

FIG. 5F is a schematic block diagram of a further illustrative, exemplary sensor diagnostic system capable of determining the value of static and dynamic physical stimuli in a transmission mode employing a MEMS-tunable VCSEL as an optical excitation source and a photodiode or similar simple device as a detector. In said illustrative example, said tunable VCSEL 30 is assembled with necessary means to fiber couple 41 the emitted light, and also to couple the VCSEL assembly 40 to an external fiber 44 to convey the laser light to an optical sensor or sensor array 45 in a transmission mode and to a reference fiber length 51 (serving as an arm of an interferometer) disposed between said VCSEL assembly and an optical sensor or sensor array 45. One or two reflection means (43 and 52) may be disposed in a reference fiber length to create a reference optical length in a fiber 51. Light transmitted through the sensor array 45 and reference fiber length 51 is then directed to the photodetector 48, causing optical interference-caused beating in the electrical signal from photodetector 48, which is transferred to the control block circuitry 49 and external electronic circuitry as required. The control block 49 may or may not control the laser temperature via a thermoelectric element or other means and may or may not adjust the laser power output according to a signal from a monitor photodiode 39, as required.

FIG. 5F shows an example illustrative implementation of a diagnostic system 40 including a MEMS-tunable VCSEL 30, a fiber light coupling means 41, an optical isolator disposed between said tunable VCSEL and either the reference fiber length or sensor array (whichever is closer), an exterior fiber 44 and a coupling means to the sensor or sensor array 45, an exit fiber 46, and a reference fiber length 51 defined by one (52) or two (52 and 43) reflective means. In this implementation, the reference fiber length is disposed in the light path connecting the tunable VCSEL, sensor array and photodetector (unlike the first aspect of the present implementation, where it was disposed on a physically separate path). Such a diagnostic system is simpler, but may degrade the isolation of the reference path from the physical stimuli imposed on the sensor array, thus may be less accurate. Other aspects of this implementation are the same as in the first aspect of this implementation, as drawn in FIG. 5E.

In preferred implementations illustrated in FIGS. 2A and 5A–F, the fiber 44 and the sensor array 45 may be bonded to or embedded in a structure which is being monitored for a perturbation change, such as dynamic or static strain and/or temperature and/or pressure and/or electrical current/or magnetic field. The structure may be made of metal, plastic, composite, or any other materials and the sensors may be disposed on or within the structure.

Figure 6A:
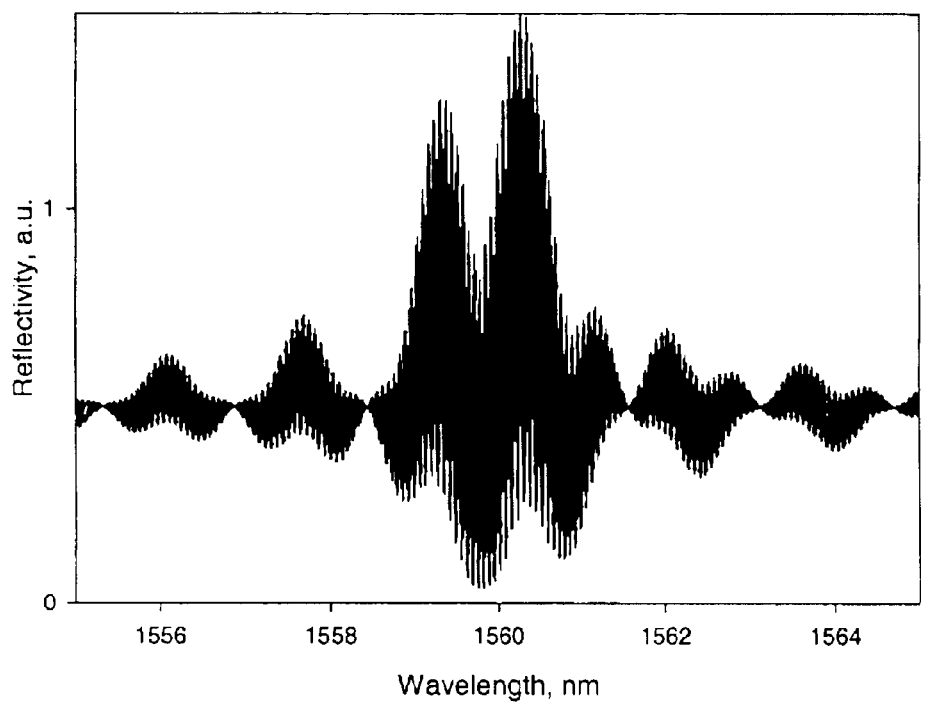
Figure 6B:
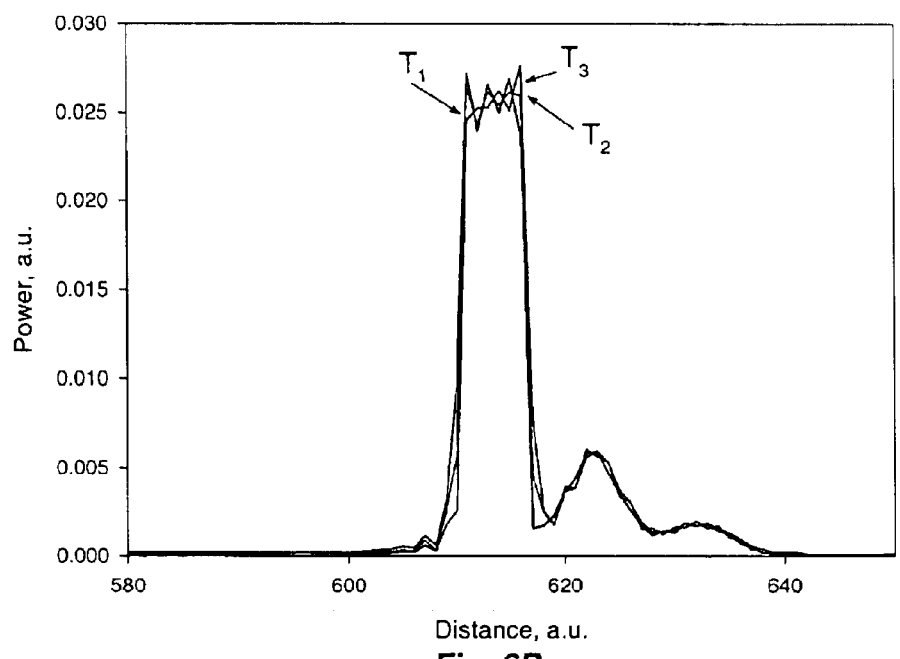
Figure 7B:
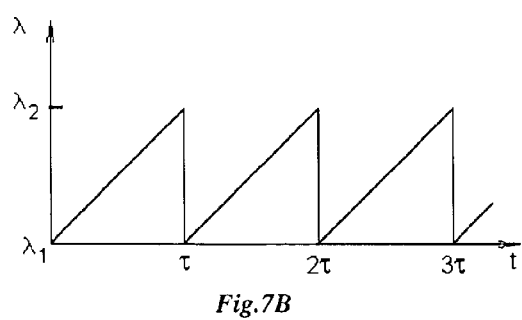
Figure 7D:
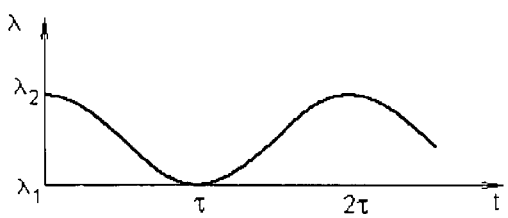
Figure 7E:
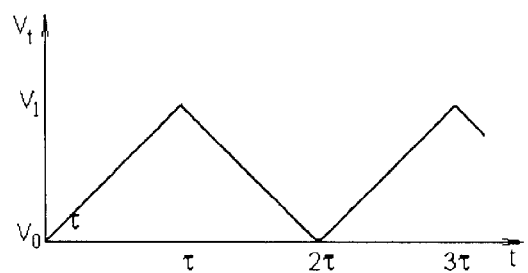
Figure 7F:
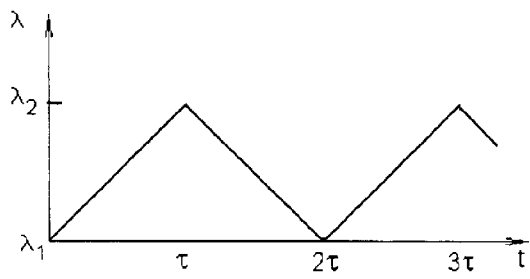

FIG. 6A shows an exemplary plot of numerically calculated reflection spectrum such as obtained in a diagnostic system of FIG. 5A when interrogating the sensor array consisting of 3 FBGs with peak Bragg wavelength of 1560 nm. FIG. 6B shows exemplary plots of a section of numerically calculated Fourier transformations of a reflection spectra from the sensor array of FIG. 6A at 3 different temperatures (0° C., 20° C., 40° C.) due to one of the FBGs in the array. FIG. 6C shows exemplary plots of numerically calculated inverse Fourier transforms of spectra of FIG. 6B.

In the illustrative implementation, the control block 49, in cooperation with additional signal processing circuitry, determines the static or dynamic value of the sensor stimulus by determining at what wavelengths the maxima or minima in signal level occur and determining the amount of change in wavelength from the wavelength maxima or minima of the unperturbed sensors. The relationship between a change in the stimulating parameter and a corresponding change in wavelength may be determined by a calibration procedure. The wavelength value is determined by monitoring the wavelength control signal and comparing it to the wavelength reference 43 or position feedback 35 of the mirror 32 (a capacitive means in this nonlimiting example), as required. Because the comparison signal is directly related to the wavelength of the tunable VCSEL 30, it provides a directly proportional value of the instantaneous wavelength. Many computation algorithms known to those skilled in the art can perform the determination of wavelength position of the minima or maxima. The ability to calculate the position of an extremum from relatively few data points enables enhanced accuracy with lower computational overhead.

Signal processing circuits (FIGS. 3A, 5A–F) analyze the electrical signals and provide a plurality of output electrical perturbation signals indicative of the perturbations being measured by the sensors within the structure. In the implementations illustrated in FIGS. 3A and 5A–F, the wavelength tuning control circuitry in control block 49 may include a function generator in order to produce the control signal waveforms in illustrated in FIGS. 7A–F. FIGS. 7A–F are a series of graphs showing exemplary, illustrative time-varying tuning control signals, represented by $V_t$, applied to the tuning mechanism of a MEMS-tunable VCSEL 30. The output wavelength, $\lambda$, as a function of time is shown as well. The waveforms shown are a sawtooth waveform (7A–7B), sinusoidal waveform (7C–7D) and triangular waveform (7E–7F), but many others could be used, including filtered waveforms designed to prevent electrical noise from affecting the tuning accuracy. Wavelength versus time should desirably be known accurately, and the linear triangle wave (7E–7F) would be superior from that point of view. The triangle waveform also allows reading all sensors 45 twice per cycle. In the exemplary implementation, the control signal $V_t$ relates directly to the expansion or contraction of the cavity 38 in the VCSEL 30, thereby causing the wavelength $\lambda$ of the output light to vary in proportion to the applied control signal $V_t$.

The triangle waveform (FIGS. 7E–7F), although providing linear dependence of the wavelength vs. time, has the disadvantage of having a discontinuity in the waveform that will by its nature induce higher frequencies, or ringing, into the system. The ringing can be filtered out by various means known in the art, but a penalty is paid in time and efficiency. The sinusoidal control signal will provide frequency stability and power-conserving scanning with much faster scanning rates due to the elimination of the stabilizing time required of a mechanical structure when a discontinuous forcing function is applied, such as the triangle wave. With the sinusoidal waveform, the entire scan can occur in a few microseconds or shorter time. This is at least a two order of magnitude speed advantage over conventional lasers, allowing better statistical averaging techniques to be used and opening the range of application requiring fast sample rates (such as strain monitoring in aircraft wings, etc.) to the diagnostic system of the exemplary non-limiting illustrative arrangement.

Instead of relying on the tuning control signal or feedback from a cantilever or diaphragm position monitoring means, such as capacitance, to calibrate the VCSEL wavelength against time, an additional unstrained or unperturbed reference means in the form of at least one Bragg grating, Fabry-Perot etalon or gas absorption cell may be inserted into the optical path. Said reference grating or cell must cause at least one reflection peak or absorption valley within the tuning range while not interfering with any sensor wavelength band, and may provide multiple extrema at $\lambda_{ref\,1}, \lambda_{ref\,2}, \lambda_{ref\,3}, \ldots \lambda_{ref\,n}$, that are always located at the same wavelength positions. Knowledge of the predetermined cycle rate, or waveform, of the voltage or other tuning signal, together with such reference wavelengths, provides the signal processing circuit with sufficient information to synchronize the beginning of each new tuning cycle with the laser wavelength. The number of wavelength reference points is determined by the accuracy and linearity of the laser tuning mechanism and the required accuracy of the physical parameter measurement. The fewest reference points will provide the most economical system. In place of a reference Bragg grating or gratings, a number of high finesse Fabry-Perot cavity filters could be used. Another applicable method of maintaining wavelength accuracy would be to place an acetylene cell in the optical path. Acetylene exhibits a number of very sharp absorption peaks in the communications wavelength bands that can be used to calibrate the system on every cycle or every half cycle. Other techniques may also be employed to maintain calibration accuracy to needed levels by those skilled in the art.

Even though the implementations have been most frequently described as using Bragg gratings as the sensors that detect the environmental stimulus, any reflective or transmissive device having a narrow reflection or transmission wavelength band, or any other reflection or transmission spectral peculiarity that shifts with applied physical stimuli may be used. Some examples of such sensors include Fabry-Perot cavity pressure, temperature and/or displacement sensors.

Referring to Bragg grating sensors, the sensors 45 need not be written into the same type of fiber 44 as the fiber that conducts light to the sensors, e.g., the sensors can be spliced into the fiber 44 or they can be separate planar chips, optically coupled to the fiber by means commonly known in the art.

Further, the implementations have been described as employing an optical fiber 44, but any other form of optical waveguide may be used if desired.

Also, it should be understood that the tuning control circuit 49 and subsequent signal processing could be done with any degree of combination of software and hardware by many methods known in the art.

Although the invention has been described and illustrated with respect to the exemplary implementations thereof, it should be understood by those skilled in the art that the foregoing and various other changes, omissions and additions may be made without departing from the scope of the invention.

We claim:

1. An optical sensor diagnostic system, comprising:
    a tunable VCSEL incorporating an integrated MEMS wavelength tuner that provides wavelength-tunable light in response to a tuning control signal;
    an optical waveguide optically coupled to said VCSEL, said tunable light being launched into said optical waveguide;
    at least one optical sensor disposed in the path of said tunable light, said tunable VCSEL individually illuminating said sensor, said sensor providing a transmitted light having altered amplitude and/or phase at least over some wavelengths within the transmitted wavelength range, said spectral distribution of said altered amplitude and/or phase being responsive to an environmental stimulus;
    an optical reference path to be optically compared with the sensing path;
    an optical detector, disposed in the path of said transmitted light, for detecting said transmitted light from said sensor and the optical reference path and for providing an electrical detection signal indicative of the power of said transmitted light throughout the appropriate wavelength range;
    a controller coupled to said tunable VCSEL, said controller providing a variable tuning control signal to said tunable VCSEL indicative of the desired wavelength of said tunable light;
    a capacitive or optical reference that determines the wavelength of the light emitted by said tunable VCSEL as a function of time and providing feedback; and
    a signal processor responsive to said electrical detection signal, for detecting a wavelength defined on the characteristic transmission amplitude feature in order to quantitatively detect the effect on said sensor due to said environmental stimulus, for detecting changes in said wavelength at the characteristic transmission amplitude feature caused by changes in said environmental stimulus, and for providing a signal indicative of said stimulus or change therein for said sensor.

2. The optical sensor diagnostic system of claim 1 wherein at least one wavelength reference independent of said tuning control signal and moveable mirror position detecting is disposed in the path of the light.

3. The optical sensor diagnostic system of claim 2 wherein at least one wavelength reference, not affected by any environmental stimulus, comprising at least one of the group of a Bragg grating, a phase shift Bragg grating, a Fabry-Perot etalon or a gas-containing chamber, is disposed in the optical path.

4. The optical sensor diagnostic system of claim 3 wherein the gas-containing chamber contains acetylene gas.

5. The optical sensor diagnostic system of claim 1 wherein optical isolation is disposed in the path of said tunable light between said tunable VCSEL and said sensor for isolating said tunable light source from light reflected from said sensor.

6. The optical sensor diagnostic system of claim 1 wherein said interferometer reference path is disposed in the path of said tunable light between said tunable VCSEL and said sensor.

7. The optical sensor diagnostic system of claim 6 wherein said interferometer reference path comprises a section of an optical fiber having the optical length chosen to provide maximum resolution of the optical sensor diagnostic system.

8. The optical sensor diagnostic system of claim 7 wherein said section of an optical fiber is defined by one or two reflectors disposed along the reference path.

9. The optical sensor diagnostic system of claim 8 wherein one of said reflectors is the part of one of the sensor.

10. The optical sensor diagnostic system of claim 1 wherein said optical detector comprises a photodiode.

11. The optical sensor diagnostic system of claim 1 wherein said interferometer reference path is disposed in the path of said tunable light between said sensor and said optical detector.

12. The optical sensor diagnostic system of claim 1 wherein said interferometer reference path comprises a section of an optical fiber having the optical length chosen to provide maximum resolution of the optical sensor diagnostic system.

13. The optical sensor diagnostic system of claim 12 wherein said section of an optical fiber is defined by one or two reflectors disposed along the reference path.

14. The optical sensor diagnostic system of claim 13 wherein one of said reflectors is the part of one of the sensor.

15. The optical sensor diagnostic system of claim 1 wherein said interferometer reference path is physically separate from the optical path that connects the VCSEL, sensor array and optical detectors and constitutes a section of an optical fiber having the optical length chosen to provide maximum resolution of the optical sensor diagnostic system is provided within the reference path.

16. The optical sensor diagnostic system of claim 15 wherein an optical splitter is disposed in the path of said tunable light between said tunable VCSEL and said at least one sensor, for splitting the light into two physically separate optical paths, one directing light toward the sensor or sensor array and another directing the light to the interferometer reference path.

17. The optical sensor diagnostic system of claim 15 wherein an optical combiner is disposed in the path of said tunable light between said tunable VCSEL and optical detector, for combining the light transmitted through the said at least one sensor and through the said interferometer reference optical path.

18. The optical sensor diagnostic system of claim 15 wherein said section of an optical fiber is defined by one or two reflector disposed along the reference path.

19. The optical sensor diagnostic system of claim 15 wherein a variable time delay device is disposed along the said interferometer reference path.

20. The optical sensor diagnostic system of claim 15 wherein a frequency shifter is disposed along the said interferometer reference path.

21. The optical sensor diagnostic system of claim 1 wherein said at least one sensor comprises at least one fiber or planar Bragg grating.

22. The optical sensor diagnostic system of claim 21 wherein at least one Bragg grating of at least one sensor comprises at least one incorporated phase shift in its structure, said phase shift producing a sharper maximum within said transmitted wavelength band minimum.

23. The optical sensor diagnostic system of claim 1 wherein said at least one sensor comprises at least one Fabry-Perot etalon.

24. The optical sensor diagnostic system of claim 23 wherein said at least one Fabry-Perot etalon comprises a section of the fiber between two Bragg gratings having the same periods or periods close enough together for the required sensing accuracy.

25. The optical sensor diagnostic system of claim 1 wherein said environmental stimulus is any combination of mechanical stress, temperature, pressure, electrical current, electrical field, magnetic field, chemical or biological effect on said sensor.

26. The optical sensor diagnostic system of claim 1 wherein at least one of said sensors serves as an environment reference or compensation sensor.

27. The optical sensor diagnostic system of claim 1 wherein at least some of said optical sensors are wavelength division multiplexed.

28. The optical sensor diagnostic system of claim 1 wherein said voltage or other controller comprises a modulator for modulating said voltage control signal at a predetermined modulation frequency.

29. The optical sensor diagnostic system of claim 1 wherein:
    said voltage or other controller comprises means for scanning said control signal for the purpose of causing said tunable VCSEL to scan its wavelengths across said characteristic transmission amplitude and/or phase features of any or all of said sensor; and
    said signal processor comprises means responsive to said voltage or other control signal for determining the wavelength of said tunable light from the magnitude of said voltage or other control signal and/or mirror position feedback signal and for determining which of said sensor is being illuminated, thereby determining the value of the environmental stimulus at the position of said individual sensor.

30. The optical sensor diagnostic system of claim 1 wherein:
    said voltage or other controller comprises means for scanning said control signal so as to cause said tunable VCSEL to scan across the characteristic transmission amplitude and/or phase features of all of said sensor and for providing a synchronization signal indicative of when said voltage control signal begins and ends said scanning; and
    said signal processor comprises means responsive to said synchronization signal for determining which of said sensor is being illuminated, thereby determining the value of the environmental stimulus at the position of said individual sensor.

31. The optical sensor diagnostic system of claim 1 wherein said signal processor comprises a demodulator operating at said modulation frequency, for demodulating said electrical detection signal and for providing a demodulated signal indicative thereof.

32. The optical sensor diagnostic system of claim 1 wherein said signal processor includes:
    digitizing the read values from the optical detector;
    forming data arrays comprising the digitized reading values, and
    producing a discrete Fourier Transform based on the digitized read values and wavelengths at which said read values have been taken;
    determining the spatial domain waveform from the said discrete Fourier Transform, and determining the value of the environmental stimulus at the position of each individual sensor.

33. The optical sensor diagnostic system of claim 32 wherein filtering of the discrete Fourier Transform is performed such that the Fourier coefficients at low frequencies and at high frequencies are set substantially to zero.

34. The optical sensor diagnostic system of claim 32 wherein the signal processor incorporates computational means for increasing the accuracy and precision of determining the value of the environmental stimulus at the position of each individual sensor.

35. The optical sensor diagnostic system of claim 1 wherein said signal processor include:
digitizing the read values from the optical detector;
forming data arrays comprising the digitized reading values, and
producing a discrete Fourier Transform based on the digitized read values and wavelengths at which said read values have been taken;
performing filtering of the discrete Fourier Transform spectra;
producing a discrete Inverse Fourier Transform based on the filtered discrete Fourier Transform spectra, and
determining the value of the environmental stimulus at the position of each individual sensor.

36. The optical sensor diagnostic system of claim 35 wherein filtering of the discrete Fourier Transform is performed such that the Fourier coefficients at low frequencies and at high frequencies are set substantially zero.

37. The optical sensor diagnostic system of claim 35 wherein the signal processor incorporates computational means for increasing the accuracy and precision of determining the value of the environmental stimulus at the position of each individual sensor.

38. The optical sensor diagnostic system of claim 35 wherein the value of the environmental stimulus at the position of each individual sensor is determined from the difference in the current wavelength position of said characteristic transmission amplitude and/or phase features and the digitally stored value of said wavelength position of said characteristic transmission amplitude.

39. An optical sensor diagnostic system, comprising:
a VCSEL incorporating an integrated MEMS wavelength tuner for providing wavelength-tunable light in response to a tuning control signal, said tunable light being launched into an optical waveguide,
at least one optical sensor, disposed in the path of said tunable light, said tunable VCSEL illuminating said sensor, said sensor providing a reflected light having altered amplitude and/or phase at least over some wavelengths within the reflected wavelength range, said spectral distribution of said altered amplitude and/or phase being responsive to an environmental stimulus imposed thereupon;
an optical reference path;
an optical divider, disposed in the path of said tunable light between said tunable VCSEL and said sensor, for directing said tunable light from said VCSEL to said sensor and in addition to said optical reference path and for redirecting the light reflected from said sensor and from said optical reference path to said detector;
an optical detector, disposed in the path of said reflected light, for detecting said reflected light from each of said sensor and for providing an electrical detection signal indicative of the power of said reflected light throughout the appropriate wavelength range;
a voltage or other controller for providing a variable tuning control signal to said tunable VCSEL indicative of the desired wavelength of said tunable light;
a capacitive, piezoresistive or optical arrangement for identification of the wavelength of the light emitted by said tunable VCSEL and providing feedback; and
a signal processor responsive to said electrical detection signal, for detecting a wavelength defined by the characteristic reflection amplitude feature in order to quantitatively detect the effect on said sensor due to said environmental stimulus, changes in said wavelength at the characteristic reflection amplitude feature caused by changes in said environmental stimulus, and for providing a signal indicative of said stimulus or change therein for said sensor.

40. The optical sensor diagnostic system of claim 39 wherein at least one wavelength reference independent of said tuning control signal and moveable mirror position detector is disposed in the path of the light.

41. The optical sensor diagnostic system of claim 40 wherein at least one wavelength reference, not affected by any environmental stimulus, comprising at least one of the group of a Bragg grating, a phase shift Bragg grating, a Fabry-Perot etalon or a gas-containing chamber, is disposed in the optical path.

42. The optical sensor diagnostic system of claim 41 wherein the gas-containing chamber contains acetylene gas.

43. The optical sensor diagnostic system of claim 39 wherein said optical divider comprises an optical coupler.

44. The optical sensor diagnostic system of claim 43 wherein optical isolator is disposed in the path of said tunable light between said tunable VCSEL and said divider, for isolating said tunable light source from light reflected from the sensor.

45. The optical sensor diagnostic system of claim 39 wherein said optical divider comprises an optical circulator.

46. The optical sensor diagnostic system of claim 39 wherein said optical reference path is disposed in the path of said tunable light between said tunable VCSEL and said sensor.

47. The optical sensor diagnostic system of claim 46 wherein said optical reference path comprises a section of an optical fiber having its optical length chosen to provide maximum resolution of the optical sensor diagnostic system.

48. The optical sensor diagnostic system of claim 47 wherein said section of an optical fiber is defined by one or two reflector disposed along the reference path.

49. The optical sensor diagnostic system of claim 48 wherein one of said reflector is a part of one of the sensor.

50. The optical sensor diagnostic system of claim 39 wherein said optical detector comprises a photodiode.

51. The optical sensor diagnostic system of claim 39 wherein said optical reference path is physically separate from the optical path connecting the VCSEL, sensor array and optical detector and a section of optical fiber having its optical length chosen to provide maximum resolution of the optical sensor diagnostic system is provided within the reference path.

52. The optical sensor diagnostic system of claim 51 wherein an optical splitter is disposed in the path of said tunable light between said tunable VCSEL and said at least one sensor, for the purpose of splitting the light into two physically separate optical paths, one directing light toward the sensor or sensor array and another to the optical reference path.

53. The optical sensor diagnostic system of claim 51 wherein an optical combiner is disposed in the path of said tunable light between said optical sensor and optical detector, for combining the light reflected from the said at least one sensor and from the said optical reference path.

54. The optical sensor diagnostic system of claim 51 wherein said section of an optical fiber is defined by one or two reflector disposed along the reference path.

55. The optical sensor diagnostic system of claim 51 wherein a variable time delay means is disposed along the said reference path.

56. The optical sensor diagnostic system of claim 51 wherein a frequency shifter is disposed along the said reference path.

57. The optical sensor diagnostic system of claim 51 wherein said at least one sensor comprises at least one fiber or planar Bragg grating.

58. The optical sensor diagnostic system of claim 57 wherein at least one Bragg grating of at least one sensor comprises at least one incorporated phase shift in its structure, said phase shift producing a sharper minimum within said reflected wavelength band maximum.

59. The optical sensor diagnostic system of claim 39 wherein said at least one sensor comprises at least one Fabry-Perot etalon.

60. The optical sensor diagnostic system of claim 59 wherein said at least one Fabry-Perot etalon comprises section of the fiber between two Bragg gratings having the same or close enough periods.

61. The optical sensor diagnostic system of claim 39 wherein said environmental stimulus is any combination of mechanical stress, temperature, pressure, electrical current, electrical field or magnetic field on said sensor.

62. The optical sensor diagnostic system of claim 39 wherein at least one of said sensors serves as an environment reference or compensation sensor.

63. The optical sensor diagnostic system of claim 39 wherein at least some of said optical sensors are wavelength division multiplexed.

64. The optical sensor diagnostic system of claim 39 wherein said voltage or other controller comprises modulator for modulating said voltage control signal at a predetermined modulation frequency.

65. The optical sensor diagnostic system of claim 39 wherein:
said voltage or other controller comprises means for scanning said control signal for the purpose of causing said tunable VCSEL to scan its wavelengths across said characteristic reflection amplitude and/or phase features of any or all of said sensor; and
said signal processor comprises means responsive to said voltage or other control signal for determining the wavelength of said tunable light from the magnitude of said voltage or other control signal and/or mirror position feedback signal and for determining which of said sensor is being illuminated, thereby determining the value of the environmental stimulus at the position of said individual sensor.

66. The optical sensor diagnostic system of claim 39 wherein:
said voltage or other controller comprises means for scanning said control signal so as to cause said tunable VCSEL to scan across the characteristic reflection amplitude and/or phase features of all of said sensor and for providing a synchronization signal indicative of when said voltage control signal begins and ends said scanning; and
said signal processor comprises means responsive to said synchronization signal for determining which of said sensor is being illuminated, thereby determining the value of the environmental stimulus at the position of said individual sensor.

67. The optical sensor diagnostic system of claim 39 wherein said signal processor comprises demodulator operating at said modulation frequency, for demodulating said electrical detection signal and for providing a demodulated signal indicative thereof.

68. The optical sensor diagnostic system of claim 39 wherein said signal processor include:
digitizing the read values from the optical detector;
forming data arrays comprising the digitized read values;
producing a discrete Fourier Transform based on the digitized read values and wavelengths at which said read values have been taken;
determining the spatial domain waveform from the said discrete Fourier Transform, and
determining the value of the environmental stimulus at the position of each individual sensor.

69. The optical sensor diagnostic system of claim 68 wherein filtering of the discrete Fourier Transform is performed such as the Fourier coefficients at low frequencies and at high frequencies are set adequately near zero.

70. The optical sensor diagnostic system of claim 68 wherein the signal processor incorporates computational means for increasing the accuracy and precision of determining the value of the environmental stimulus at the position of each individual sensor.

71. The optical sensor diagnostic system of claim 39 wherein said signal processor include:
digitizing the read values from the optical detector;
forming arrays comprising the digitized read values;
producing a discrete Fourier Transform based on the digitized read values and wavelengths at which said read values have been taken;
perform filtering of the discrete Fourier Transform spectra;
producing a discrete Inverse Fourier Transform based on the filtered discrete Fourier Transform spectra, and
determining the value of the environmental stimulus at the position of each individual sensor.

72. The optical sensor diagnostic system of claim 71 wherein filtering of the discrete Fourier Transform is performed such that the Fourier coefficients at low frequencies and at high frequencies are set substantially to zero.

73. The optical sensor diagnostic system of claim 71 wherein the signal processor incorporates computational means for increasing the accuracy and precision of determining the value of the environmental stimulus at the position of each individual sensor.

74. The optical sensor diagnostic system of claim 71 wherein the value of the environmental stimulus at the position of each individual sensor is determined from the difference in the current wavelength position of said characteristic reflection amplitude features and a digitally stored value of said wavelength position of said characteristic reflection amplitude features.

75. The optical sensor diagnostic system of claim 39 wherein at least one sensor is disposed in a branch waveguide or optical fiber coupled to the main waveguide.

76. An optical sensor diagnostic method comprising:
tuning an on-chip tunable VCSEL to provide wavelength-tunable light, including providing a variable tuning control signal to said tunable VCSEL indicative of a desired wavelength of said tunable light and providing feedback responsive at least in part to the wavelength of the light emitted by said tunable VCSEL;

directing some of said tunable light from said VCSEL to at least one optical sensor to illuminate said sensor with said tunable light, said sensor providing a reflected light having altered amplitude and/or phase at least over some wavelengths within a reflected wavelength range, said spectral distribution of said altered amplitude and/or phase being responsive to an environmental stimulus imposed upon said sensor;

directing some of said tunable light along an optical reference path;

redirecting at least some of the light reflected from said sensor and from said optical reference path to an optical detector;

detecting, with said optical detector, said reflected light from said sensor and providing an electrical detection signal indicative of the power of said reflected light throughout the reflected wavelength range; and detecting a wavelength defined by a characteristic reflection amplitude feature to quantitatively detect the effect on said sensor due to said environmental stimulus, changes in said wavelength at the characteristic reflection amplitude feature caused by changes in said environmental stimulus, and providing a signal indicative of said stimulus or change therein for said sensor.

* * * * *